United States Patent [19]

Girten et al.

[11] Patent Number: 5,726,156
[45] Date of Patent: Mar. 10, 1998

[54] CYTOKINE REGULATORY AGENTS AND METHODS OF USE IN PATHOLOGIES AND CONDITIONS ASSOCIATED WITH ALTERED CYTOKINE LEVELS

[75] Inventors: Beverly E. Girten; Ali Andalibi; Amaresh Basu, all of San Diego; Patrick Fagan, Escondido; Richard A. Houghten, Del Mar; Costas C. Loullis, Cardiff; Paul Omholt, San Diego; Ronald R. Tuttle, Escondido; Mark J. Suto, San Diego, all of Calif.; Patricia A. Weber, Stevensville, Mont.

[73] Assignee: Trega Biosciences, Inc., San Diego, Calif.

[21] Appl. No.: 527,056

[22] Filed: Sep. 12, 1995

Related U.S. Application Data

[63] Continuation-in-part of Ser. No. 484,262, Jun. 7, 1995, abandoned, which is a continuation-in-part of Ser. No. 400,983, Mar. 6, 1995.

[51] Int. Cl.$^6$ ..................................................... A61K 38/00
[52] U.S. Cl. ............................. 514/16; 514/17; 514/18; 530/317; 530/322; 530/329; 530/330
[58] Field of Search ................................ 514/16, 17, 18; 530/317, 322, 329, 330

[56] References Cited

U.S. PATENT DOCUMENTS

| | | | |
|---|---|---|---|
| 4,457,864 | 7/1984 | Hruby et al. | 260/112.5 |
| 4,485,039 | 11/1984 | Hruby et al. | 260/112.5 R |
| 4,649,191 | 3/1987 | Hruby | 530/329 |
| 4,866,038 | 9/1989 | Hruby et al. | 514/14 |
| 4,918,055 | 4/1990 | Hruby et al. | 514/14 |
| 5,028,592 | 7/1991 | Lipton | 514/18 |
| 5,049,547 | 9/1991 | Hruby et al. | 514/14 |
| 5,157,023 | 10/1992 | Lipton | 514/18 |
| 5,408,038 | 4/1995 | Smith et al. | 530/359 |
| 5,420,109 | 5/1995 | Suto et al. | 514/8 |
| 5,462,927 | 10/1995 | Moreau | 514/17 |

FOREIGN PATENT DOCUMENTS

| | | |
|---|---|---|
| 0 292 291 | 5/1988 | European Pat. Off. . |
| 0 427 458 | 5/1991 | European Pat. Off. . |
| 0427458 | 5/1991 | European Pat. Off. . |
| 0 568 925 | 4/1993 | European Pat. Off. . |
| 2691465A1 | 11/1993 | France . |
| WO 87/04623 | 3/1987 | WIPO . |

OTHER PUBLICATIONS

Dayhoff, *Atlas of Protein Sequence and Structure*, vol. 5, 1972, p. 96.

Abou–Mohamed et al., "HP–228, a novel synthetic peptide, inhibits the induction of nitric oxide synthase in vivo but no in vitro." *J. Pharmacol. Exp. Ther.*, 275(2):584–591 (Jul. 21, 1995).

Dinarello et al., "The role of interleukin–1 in disease." *New England J. Med.*, 328:106–113 (1993).

Richards and Lipton, "Effect of α–MSH 11–13 (Lysine–Proline–Valine) on Fever in the Rabbit." *Peptides*, 5:815–817 (1984).

Deeter et al., "Antipyretic properties of centrally administered α–MSH fragments in the rabbit." *Peptides* 9:1285–1288 (1989).

Sugg et al., "D–Isomeric replacements within the 6–9 core sequence of a Ac-[Nle$^4$]–α–MSH$_{4-11}$–NH$_2$: A topological model for the solution conformation of α–Melanotropin." *Biopolymers*, 25:2029–2042 (1986).

Norlund, James J., "α–Melanocyte–stimulating hormone a ubiquitous cytokine with pigmenting effects." *J. Amer. Med. Assoc.*, 226:2753–2754 (1991).

Levine et al., "Induction of skin tanning by subcutaneous administration of a potent synthetic melanotropin." *J. Amer. Med. Assoc.*, 266:2730–2736 (1991).

Al–Obeidi et al., "Design of a new class of superpotent cyclic α–melanotrophins based on quenched dynamic simulations." *J. Am. Chem. Soc.*, 111:3413–3416 (1989).

Poole et al., "Peripheral analgesic activities of peptides related to α–melanocyte stimulating hormone and interleukin–1β$^{193-195}$." *Br. J. Pharmacol.* 106:489–492 (1992).

Follenfant et al., "Inhibition by neuropeptides of interleukin–1 β–induced prostaglandin–independent hyperalgesia." *Br. J. Pharmacol.*, 98:41–43 (1989).

Rivier et al., "In the mouse, the activation of the hypothalamic–pituitary–adrenal axis by a lipopolysaccharide (Endotoxin) is mediated through interleukin–1." *Endocrinology*, 125(60):2800–2805 (1989).

Vinegar et al., "Biphasic development of carrageenin edema in rats." *J. of Pharmacol. and Exper. Therapeutics*, 166(1):96–103 (1969).

Vinegar et al., "Pathway to carrageenan–induced inflammation in the hind limb of the rat." *Federation Proc.*, 46:118–126 (1987).

Hiltz and Lipton, "Alpha–MSH peptides inhibit acute inflammation and contact sensitivity." *Peptides*, 11(5):979–982 (1990).

(List continued on next page.)

*Primary Examiner*—Cecilia J. Tsang
*Assistant Examiner*—C. Delacroix-Muirheid
*Attorney, Agent, or Firm*—Campbell & Flores LLP

[57] ABSTRACT

The present invention relates to novel peptides that are potent cytokine regulatory agents. In addition, the present invention relates to pharmaceutical compositions comprising a pharmaceutically acceptable carrier and a cytokine regulatory agent. Administration of such a cytokine regulatory agent to a subject can enhance or restrain cytokine activity. Thus, the present invention provides a method of regulating cytokine activity in a subject having a condition characterized by aberrant or altered cytokine activity. The invention also provides methods of treating such conditions, including, for example, disuse deconditioning, diseases mediated by nitric oxide and cytokines, adverse drug reactions, obesity, septic shock, and adverse side effects due to cancer chemotherapy or occurring as in response to organ transplantation.

31 Claims, 4 Drawing Sheets

OTHER PUBLICATIONS

Ray et al., "Cytokines and their receptors: Molecular mechanism of interleukin–6 gene repression by glucocorticoids." *J. Am. Soc. Nephrol.*, 2:S214–S221 (1992).

Karkar et al., "Passive immunization against tumor necrosis factor–alpha (TNF–α) and IL–1β protects from LPS enhancing glomerular injury in nephrotoxic nephritis in rats." *Clin. Exp. Immunol.*, 90:312–318 (1992).

Ulich et al., "Indotoxin–induced cytokine gene expression in vivo." *Am. J. of Pathol.*, 141(1):61–68 (1992).

Jansen et al., "Induction of nitric oxide synthase in rat immune complex glomerulonephritis." *Kidney Int'l.*, 45:1215–1219 (1994).

Mackensen et al., "Treatment of cancer patients with endotoxin induces release of endogenous cytokines." *Pathobiol.*, 59:264–267 (1991).

Mackensen et al., "Modulating activity of interferon–γ on endotoxin–induced cytokine production in cancer patients." *Blood*, 78(12):3254–3258 (1991).

Rabinowitz et al., "Characterization on endogenous cytokine concentrations after high–dose chemotherapy with antologous bone marrow support." *Blood*, 81(9):2452–2459 (1993).

Mosmann Tim R., "Interleukin–10." *The Cytokine Handbook*, 2nd Ed., Ch. 12 (1994).

Moore et al., "Interleukin–10." *Annu. Rev. Immunol.*, 11:165–190 (1993).

Chernoff et al., "A randomized, controlled trial of IL–10 in humans: Inhibition of inflammatory cytokine production and immune responses." *J. of Immunol.*, 154:5492–5499 (1995).

Rennick et al., "Interleukin 10: An overview." *Progress in Growth Factor Research*, 4:207–227 (1992).

Spits and Malefyt, "Funcational characterization of human IL–10." *Int. Arch. Allery Immunol.*, 99:8–15 (1992).

Cassatella et al., "Interleukin 10 (IL–10) upregulates IL–1 receptor antagonist production from lipoplysaccharide–stimulated human polymorphonuclear leukocytes by delaying mRNA degradation." *J. Exp. Med.*, 179:1695–1699 (1994).

Marchant et al., "Interleukin–10 controls interferon–γ and tumor necrosis factor production during experimental endotoxemia." *Eur. J. Immunol.*, 24:1167–1171 (1994).

Katsikis et al., "Immunoregulatory role of interleukin 10 in rheumatoid arthritis." *J. Exp. Med.*, 179:1517–1527 (1994).

Gerard et al., "Interleukin 10 reduces the release of tumor necrosis factor and prevents lethality in experimental endotoxemia." *J. Exp. Med.*, 177:547–550 (1993).

Ward et al., "Aerobic training and diabetic nephropathy in the obese zucker rat." *Annals of Clinical and Laboratory Science*, 24(3):266–277 (1994).

T.B. NG, "Studies on hormonal regulation of lipolysis and lipogenesis in fat cells of various mammalian species." *Comparative Biochem. and Phys. B: Comparative Biochem.*, 97(3):441–446 (1990).

Hotamislig and Spiegelman, "Tumor necrosis factor α: A key component of the obesity–diabetes link." *Diabetes*, 43:1271–1278 (1994).

Hotamislig et al., "Increased adipose tissue expression of tumor necrosis factor–α in human obesity and insulin resistance." *J. Clin. Invest.*, 95:2409–2415 (1995).

Hotamislig et al., "Reduced tyrosine kinase activity of the insulin receptor in obesity–diabetes: Central role of tumor necrosis factor–α." *J. Clin. Invest.*, 94:1543–1549 (1994).

Weinsier et al., "Metabolic predictors of obesity: Contribution of resting energy expenditure, themic effect of food, and fuel utilization to four–year weight gain of post–obese and never–obese women." *J. Clin. Invest.*, 95:980–985 (1995).

Creekmore et al., "Strategies for clinical monitoring of therapeutic trials." *Manual of Clin. Lab. Immunol.*, 915–922 (1992).

Thavasu et al., "Measuring cytokine levels in blood: Importance of anticoagulants, processing, and storage conditions." *J.of Immunol. Methods*, 153:115–124 (1992).

Payne et al., "Hypothalamic releasing hormones mediating the effects of interleukin–1 on sleep." *J. of Cell. Biochem.*, 53:309–313 (1993).

Tilg et al., "Interleukin–6 (IL–6) as an anti–inflammatory cytokine: Induction of circulating IL–1 receptor antagonist and soluble tumor necrosis factor receptor p55." *Blood*, 83(1):113–118 (1994).

Wong et al., "Interleukin (IL) 4 differentially regulates monocyte IL–1 family gene expression and synthesis in vitro and in vivo." *J. of Exp. Med.*, 177:775–781 (1993).

Gorgen et al., "Granulocyte colony–stimulating factor treatment protects rodents against lipopolysaccharide–induced toxicity via suppression of systemic tumor necrosis factor–α." *J. of Immunol.*, 149:918–924 (1992).

CYTOKINE REGULATORY AGENTS AND METHODS OF USE IN PATHOLOGIES AND CONDITIONS ASSOCIATED WITH ALTERED CYTOKINE LEVELS

This application is a continuation-in-part of application Ser. No. 08/484,262, filed Jun. 7, 1995 now abandoned which is a continuation-in-part of application Ser. No. 08/400,983, filed Mar. 6, 1995.

BACKGROUND OF THE INVENTION

1. Field of the Invention

The present invention relates generally to the fields of peptide chemistry and molecular pathology and, more specifically, to novel cytokine regulatory agents and their use in controlling cytokine-regulated physiologic processes and pathologies.

2. Background Information

Cytokines are a class of secreted, soluble proteins produced by a variety of cells in response to many different kinds of inducing stimuli, including environmental, mechanical, and pathological stresses. Lymphoid, inflammatory and hemopoietic cells secrete a variety of cytokines which regulate the immune response by controlling cell proliferation, differentiation and effector functions. For example, regulatory cytokines produced in response to T cell stimulation during an immune response can be immunosuppressive or immunostimulatory. The immune response and acute phase response associated with altered cytokine levels can occur, for example, due to disuse deconditioning, organ damage such as that associated with transplantation, cancer treatment, septic shock and other bacterially related pathologies, adverse drug reactions, nitric oxide mediated tissue damage and diabetes.

Cytokines are normally present in very low concentrations in a tissue and their effects are mediated through binding to high affinity receptors on specific cell types. Various cytokines such as the interleukins (IL), interferons (IFN), colony stimulating factors (CSF) and tumor necrosis factors (TNF) are produced during immune, inflammatory, repair and acute phase responses and they control various aspects of these responses. Following induction of such an immune, inflammatory, repair or acute phase response, the concentrations of various cytokines can increase or decrease at different times. For example, increased levels of cytokines are associated with a variety of situations such as space flight, immobilization, spinal cord injury, and bed rest, which result in disuse deconditioning. During space flight, for example, TNF, IL-6, and IL-2 levels increase upon a subject's initial exposure to weightlessness and again upon return from space.

Altered levels of cytokines have also been linked to abnormal bone metabolism and the rapid decalcification that occurs during immobilization, spinal cord injury, or long-term bed rest. Similarly, cytokine levels are altered during chronic states such as during repair and autoimmune reactions to organ damage, nephrotoxicity associated with the administration of cyclosporine to transplant subjects, cancer chemotherapy, as well as in individuals that are obese or suffering from diabetes, septic (endotoxic) shock or glomerulonephritis.

Cytokines, including the TNFs, CSFs, interferons and interleukins mediate host defense responses, cell regulation and cell differentiation. For example, these cytokines can induce fever in a subject, can cause activation of T cells, B cells and macrophages, and can affect the levels of other cytokines, which result in a cascade effect whereby other cytokines mediate the biological levels and actions of the first cytokine.

Cytokines may regulate the immune response through immunostimulatory or immunosuppresive effects. For example, IL-10 can block activation of many of the inflammatory cytokines including TNF, IL-1 and IL-6, while upregulating anti-inflammatory cytokines, such as IL-12. IL-10, which is produced by macrophages and other cell types, also stimulates the proliferation of mast cells and thymocytes and inhibits various functions of monocytes and macrophages. As a consequence of this monocyte and macrophage inhibition, the activity of T cells is also affected. The full scope of the role of IL-10 in the immune system is only beginning to be understood.

Cytokines have multiple biological activities and interact with more than one cell type. Thus, it has not been possible to target one particular cytokine or cell type to prevent the damaging side effects of treatment. A better approach for preventing damage due to the unwanted and uncontrolled over-suppression or over-stimulation of cytokine activity would be to regulate the expression of the relevant or controlling cytokine or cytokines involved in an immune response without eliminating or over-expressing any one cytokine. Such a treatment would not create or aggravate a pathological or ongoing immune response. In this way, pathological immune-mediated effects, such as immunosuppression or autoimmune reactions, can be prevented and homeostasis can be maintained.

Corticosteroids can be used to modulate cytokine expression. However, they can cause complete immunosuppression and have other undesirable side effects, such as inducing "wasting" syndrome, diabetes and osteoporosis. Similarly, non-steroidal anti-inflammatory drugs (NSAID), such as ketorolac (Toradol®; Syntex), are effective in treating inflammation and pain. However, NSAIDs also cause undesirable side effects by inhibiting prostaglandin production, which can lead to potentially severe complications including gastric ulceration, bleeding and renal failure.

In order to prevent pathological conditions or disruption of normal immune mediated functions caused by the aberrant expression of cytokines as described above, it would be advantageous if cytokine levels could be accurately manipulated and efficaciously controlled. Thus, a need exists for agents that can regulate the activity of cytokines in a subject without causing undesirable side effects. Furthermore, a need exists for identifying agents which can be used in the treatment of pathologies and conditions associated with altered cytokine levels. The present invention satisfies these needs and provides related advantages as well.

SUMMARY OF THE INVENTION

The present invention relates to novel peptides that are potent cytokine regulatory agents. As disclosed herein, such cytokine regulatory agents have the general structures, $X_1$-$X_2$-His-(D) Phe-Arg-(D) Trp-$X_3$, and $X_4$-$X_5$-(D) Phe-Arg-(D) Trp-$X_3$, where $X_1$, $X_2$, $X_3$, $X_4$, and $X_5$ can be amino acids or amino acid analogs. The invention also relates to a cytokine regulatory agent having the structure, Ac-His-(D) Phe-Arg-(D)Trp($CH_2$)-(NAc)Gly-$NH_2$, which contains a reduced (D) Trp analog.

In addition, the present invention relates to pharmaceutical compositions comprising a pharmaceutically acceptable carrier and a cytokine regulatory agent or agents. Administration of such a cytokine regulatory agent or a combination thereof to a subject can modify the levels of various cytokines in the individual, which will result in immunostimulation or immunosuppression depending on the particular cytokines that are regulated.

The present invention also provides methods of regulating through enhancement the cytokine activity in a subject and methods of treating a condition, pathology or an injury characterized, in part, by altered or aberrant cytokine activity. Such conditions, pathologies or injuries include disuse deconditioning, diseases mediated by nitric oxide and cytokines, diabetes, obesity, autoimmune diseases, septic (endotoxic) shock, glomerulonephritis, organ damage such as that which occurs during transplantation and adverse side effects of cancer chemotherapy, such as nephrotoxicity.

DETAILED DESCRIPTION OF THE INVENTION

Figure 1A:
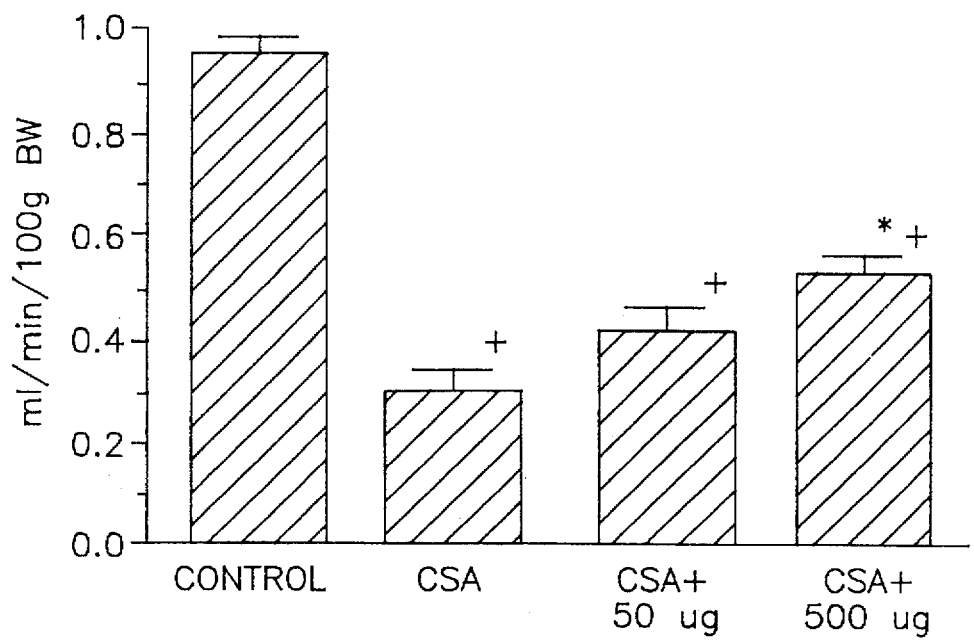
FIGS. 1a and 1b demonstrate that a cytokine regulatory agent effectively restrains the decrease in glomerular filtration rate that occurs due to cyclosporine-induced nephrotoxicity.

The present invention generally relates to novel cytokine regulatory agents having the structure: $X_1$-$X_2$-His-(D)Phe-Arg-(D)Trp-$X_3$, wherein

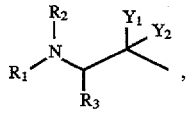

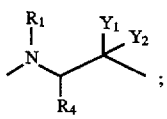

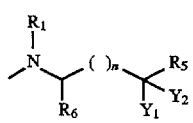

wherein $Y_1$ and $Y_2$ are independently a hydrogen atom, or are taken together to form a carbonyl or thiocarbonyl; $R_1$ is H, $COCH_3$, $C_2H_5$, $CH_2Ph$, COPh, COO-t-butyl, $COOCH_2Ph$, $CH_2CO$-(polyethylene glycol) or A; $R_2$ is H or $COCH_3$; $R_3$ is a linear or branched alkyl group having 1 to 6 carbon atoms or a cyclic alkyl group having 3 to 6 carbon atoms; $R_4$ is $(CH_2)_m$—$CONH_2$, $(CH_2)_m$—$CONHR_1$ or $(CH_2)_m$—CONHA; $R_5$ is OH, $OR_3$, $NH_2$, SH, $NHCH_3$, $NHCH_2Ph$ or A; and $R_6$ is H or $R_3$; and wherein "Ph" is $C_6H_5$; "m" is 1, 2 or 3; "n" is 0, 1, 2 or 3; and "A" is a carbohydrate having the general formula:

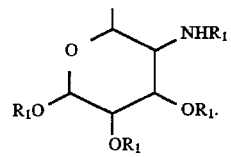

In one embodiment of the present invention, the peptides have any of the variables described above for $X_1$ and $X_2$ and specifically have OH for $X_3$ ($X_3$ is $R_5$, wherein $R_5$ is OH). In yet another embodiment, Y, $R_1$, $R_2$, $R_4$, $R_5$, and $R_6$ can be any of the variables described above and $R_3$ is a cyclic alkyl group having 3 to 6 carbon atoms.

Exemplary peptides encompassed by the formulas disclosed above include Nle-Gln-His-(D) Phe-Arg-(D) Trp-Gly-$NH_2$; Ac-Nle-Gln-His-(D)Phe-Arg-(D)Trp-Gly-$NH_2$; and Ac-(cyclohexyl)Gly-Gln-His-(D)Phe-Arg-(D)Trp-Gly-$NH_2$, each of which can regulate cytokine activity.

The present invention also relates to novel cytokine regulatory agents having the structure: $X_4$-$X_5$-(D) Phe-Arg-(D) Trp-X3, wherein

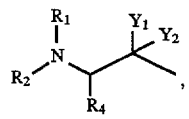

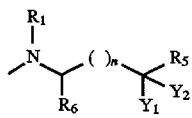

wherein Y1 and Y2 are independently a hydrogen atom, or are taken together to form a carbonyl or thiocarbonyl; $R_1$ is H, $COCH_3$, $C_2H_5$, $CH_2Ph$, COPh, COO-t-butyl, $COOCH_2Ph$, $CH_2CO$-(polyethylene glycol) or A; $R_2$ is H or $COCH_3$; $R_4$ is $(CH_2)_m$-$CONH_2$, $(CH_2)_m$-$CONHR_1$ or $(CH_2)_m$-CONHA; $R_5$ is OH, $OR_3$, $NH_2$, SH, $NHCH_3$, $NHCH_2Ph$ or A; and $R_6$ is H Or $R_3$; and wherein "Ph" is $C_6H_5$; "m" is 1, 2 or 3; "n" is 0, 1, 2 or 3; and "A" is a carbohydrate having the general formula

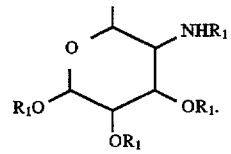

In one embodiment of the present invention, the peptides are shortened analogs of 3 to 5 amino acid residues, having any of the variables described above for $X_4$ and $X_5$ and specifically having OH for $X_3$ ($X_3$ is $R_5$, wherein $R_5$ is OH). In yet another embodiment, where $X_4$ is absent, $X_5$ is H or $COCH_3$, and $X_3$ is $R_5$, the cytokine regulatory agents are tripeptides of (D) Phe-Arg- (D) Trp. Preferred peptides include His- (D) Phe-Arg- (D) Trp-Gly-$NH_2$; Ac-His- (D) Phe-Arg- (D) Trp-$NH_2$; His- (D) Phe-Arg- (D) Trp-OH; Ac-(D) Phe-Arg-Trp-$NH_2$; and cyclo (His- (D) Phe-Arg- (D) Trp) , which can regulate cytokine activity.

As used herein, the terms "regulate" or "regulatory" mean to control by enhancing, limiting, restricting, restraining, modulating or moderating. Such regulation includes the pleiotropic, redundant, synergistic or antagonistic effects that occur due to the activity of biological agents such as cytokines, which can affect a variety of biological functions directly or indirectly through cascade or biofeedback mechanisms.

As used herein, the term "cytokine regulatory agent" means an agent that controls cytokine activity by enhancing, limiting, restricting, restraining, modulating or moderating the biological activity of a cytokine. It should be recognized, however, that while the cytokine regulating agents generally can regulate cytokine activity, no specific mechanism of action is proposed as to how a cytokine regulatory agent acts to effect a condition characterized by altered or aberrant cytokine activity.

Cytokines are well known in the art and include, but are not limited to the tumor necrosis factors (TNFs), colony stimulating factors (CSFs), interferons (INFs), interleukins (IL-1, IL-2, IL-3, IL-4, IL-5, IL-6, IL-7, IL-8, IL-9, IL-10, IL-11, IL-12, IL-13, IL-14, and IL-15), transforming growth factors (TGFs), oncostatin M (OSM), leukemia inhibiting factor (LIF), platelet activating factor (PAF) and other soluble immunoregulatory peptides that mediate host defense responses, cell regulation and cell differentiation (see, for example, Kuby, *Immunology* 2d ed. (W. H. Freeman and Co. 1994); see Chapter 13, which is incorporated herein by reference).

The cytokine regulatory agents of the invention can regulate the aberrant or altered expression of one or more cytokines that occurs in various conditions, including, for example, pathologies, immune responses and inflammatory responses. Such conditions are considered together for purposes of the present invention is that they are characterized, in part, by altered or aberrant cytokine activity and, therefore, are amenable to regulation by one or more cytokine regulatory agents.

As used herein, the term "characterized by" means contributes or affects, at least in part. Though cytokine contribution can be, it does not have to be, and the only, primary, or even a major factor of the condition. For example, it is well understood in the art that an infection has altered cytokine levels and is, therefore, a condition characterized by cytokine activity, but that cytokines activity is only a part of the infectious condition.

As used herein, the term "condition characterized by altered or aberrant cytokine activity" includes all cytokine regulated or modulated pathologies and injuries, including the immune, inflamatory and healing processes associated with an injury. The skilled artisan can recognize such a condition by detecting an increased or decreased level or activity of a particular cytokine as compared to the normal level of the cytokine expected to be found in a healthy individual. Methods for determining such normal levels are well known in the art.

Conditions characterized by altered or aberrant cytokine activity include, but are not limited to, disuse deconditioning, organ damage such as occurs in response to organ transplantation; adverse reactions associated with cancer chemotherapy; obesity; diseases such as diabetes and atherosclerosis that are mediated by free radicals and nitric oxide action; bacterial endotoxic sepsis and related shock; pain; cachexia; adult respiratory distress syndrome; and autoimmune or other patho-immunogenic diseases or reactions such as allergic reactions or anaphylaxis, arthritis, inflammatory bowel disease, glomerulonephritis, systemic lupus erythematosus, transplant atherosclerosis and parasitic mediated immune dysfunctions such as Chagas' Disease.

A cytokine regulatory agent can be, for example, a peptide comprising amino acids or amino acid analogs as described herein. In addition to the examples provided above, other representative examples of peptide cytokine regulatory agents include:

1) Ac—Nle—Gln—His—(D)Phe—Arg—(D)Trp—Gly—OH;

2) Ac—Nle—Gln—His—(D)Phe—Arg—(D)Trp—Gly—NH$_2$;

3) Ac—Nle—Gln—His—(D)Phe—Arg—(D)Trp—Gly—OC$_2$H$_5$;

4) Ac—Nle—Gln—His—(D)Phe—Arg—(D)Trp—Gly—NH—NH$_2$;

5) Ac—Nle—Asn—His—(D)Phe—Arg—(D)Trp—Gly—NH$_2$;

6) Ac—Nle—Asn—His—(D)Phe—Arg—(D)Trp—Gly—OH;

7) Ac—Nle—Gln—His—(D)Phe—Arg—(D)Trp—Gly—NHCH$_2$CH$_2$Ph;

8) Ac—Nle—Gln—His—(D)Phe—Arg—(D)Trp—Gly—NHCH$_2$Ph;

9) Nle—Gln—His—(D)Phe—Arg—(D)Trp—Gly
   |                                    |
   N ─────────────────────────────── =O;

10) Ac—Gln—His—(D)Phe—Arg—(D)Trp—Gly—NH$_2$;

11) Ac—Nle—Gln—His—(D)Phe—Arg—(D)Trp—NH$_2$;

12) Ac—His—(D)Phe—Arg—(D)Trp—Gly—NH$_2$;

13) His—(D)Phe—Arg—(D)Trp—NH$_2$;

14) Ac—His—(D)Phe—Arg—(D)Trp—OH; and

15) Ac—His—(D)Phe—Arg—(D)Trp(CH$_2$)—(NAc)Gly—NH$_2$, wherein (D) Trp (CH$_2$) is an analog of (D) Trp, where H$_2$ replaces the α-carbonyl oxygen and (NAc)Gly is a glycine derivative with an N-acetyl moiety.

Peptide cytokine regulatory agents as described above are characterized, in part, by a core structure having the amino acid sequence, (D) Phe-Arg-(D)Trp, or an analog of (D)Trp, and more preferably the core amino acid sequence His-(D) Phe-Arg-(D)Trp, or an analog of (D)Trp. The amino acids are indicated by their commonly known three letter code and (D) designates an amino acid having the "D" configuration, as opposed to the naturally occurring L-amino acids. Where no specific configuration is indicated, one skilled in the art would understand the amino acid to be an (L)-amino acid. In the peptides exemplified above, "Nle" is the three letter code for norleucine and "Ph" indicates a "phenyl" group (C$_6$H$_5$).

Cytokine regulatory agents such as the peptides described above were synthesized using a modification of the solid phase peptide synthesis method of Merrifield (*J. Am. Chem. Soc.*, 85:2149 (1964), which is incorporated herein by reference) or can be synthesized using standard solution methods well known in the art (see, for example, Bodanzsky, M., *Principles of Peptide Synthesis* 2nd revised ed. (Springer-Verlag, 1988 and 1993), which is incorporated herein by reference). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

Peptides were synthesized using amino acids or amino acid analogs, the active groups of which were protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxy methyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

One skilled in the art would know that the choice of amino acids or amino acid analogs incorporated into the peptide will depend, in part, on the specific physical, chemical or biological characteristics required of the cytokine regulatory agent. Such characteristics are determined, in part, by the route by which the cytokine regulatory agent will be administered or the location in a subject to which the activity of the cytokine regulatory agent will be directed.

Selective modification of the reactive groups in a peptide also can impart additional desirable characteristics to a cytokine regulatory agent. Peptides can be manipulated while still attached to the resin to obtain N-terminal modified compounds such as an acetylated peptide or can be removed from the resin using hydrogen fluoride or an equivalent cleaving reagent and then modified. Compounds synthesized containing the C-terminal carboxyl group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or methods for amidation of the C-terminus. Similarly, methods for modifying side chains of the amino acids or amino acid analogs are well known to those skilled in the art of peptide synthesis. The choice of modifications made to the reactive groups present on the peptide will be determined by the characteristics that the skilled artisan requires in the cytokine regulatory agent.

Particular cyclic peptides also can be an effective cytokine regulatory agent. A cyclic peptide can be obtained by inducing the formation of a covalent bond between, for example, the amino group at the N-terminus of the peptide and the carboxyl group at the C-terminus. For example, the peptide, cyclo(His-(D)Phe-Arg-(D) Trp), which can be produced by inducing the formation of a covalent bond between His and (D)Trp, can have cytokine regulatory activity. Alternatively, a cyclic peptide can be obtained by forming a covalent bond between a terminal reactive group and a reactive amino acid side chain or between two reactive amino acid side chains. One skilled in the art would know that the choice of a particular cyclic peptide is determined by the reactive groups present on the peptide as well as the desired characteristic of the peptide. For example, a cyclic peptide may provide a cytokine regulatory agent with increased stability, increased solubility, decreased immunogenicity, or decreased clearance in vivo.

A newly synthesized peptide can be purified using a method such as reverse phase high performance liquid chromatography (RP-HPLC), which is described in detail below (see Example I), or other methods of separation based on the size or charge of the peptide. Furthermore, the purified peptide can be characterized using these and other well known methods such as amino acid analysis and mass spectroscopy, which are described in detail below (see Example I).

The invention also relates to pharmaceutical compositions comprising a cytokine regulatory agent or agents and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters.

A pharmaceutically acceptable carrier can contain physiologically acceptable compounds that act, for example, to stabilize the cytokine regulatory agent or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the cytokine regulatory agent and on the particular physio-chemical characteristics of the specific cytokine regulatory agent.

A cytokine regulatory agent as described above or a pharmaceutical composition containing a cytokine regulatory agent can be administered to a subject in order to regulate pathologically modified, including depressed or elevated, cytokine activity in the subject. For example, the peptide or composition can be administered to a subject as a treatment for traumatic injuries, bacterial sepsis and endotoxic shock, inflammation, pain, cachexia, adult respiratory distress syndrome, transplant atherosclerosis, and pathoimmunogenic diseases such as arthritis, inflammatory bowel disease systemic lupus erythematosus and other autoimmune dysfunctions, each of which is characterized by pathologically elevated inflammatory cytokine activity.

As used herein, the term "pathologically elevated" means that a cytokine activity is elevated above a range of activities which is expected in a normal population of such subjects and which is associated with a pathological response. For example, a normal range of IL-1, such as IL-1β, activity present in a specific tissue can be determined by sampling a number of subjects in the population. A subject having a pathology characterized by cytokine-induced pathological effects can be readily identified by determining that the cytokine activity in the subject is pathologically elevated, which is above the normal range and which results in a pathological response such as a fever.

In addition, as described in more detail below, the peptides or pharmaceutical compositions can also be used for treating obesity, disuse deconditioning and diseases mediated by nitric oxide, such as diabetes and glomerulonephritis, transplant atherosclerosis, multiple sclerosis, as well as for reducing the negative effects of a cancer chemotherapeutic agent, and for protecting organs against damage, induced by chemotherapeutic, antifungal (amphotericin), antibacterial (aminoglycoside antibiotics), and antiviral (azidothymidine) agents, all of which are associated with pathologically altered levels of cytokines.

Disuse Deconditioning

Altered levels of cytokines are associated with a variety of conditions that lead to disuse deconditioning, such as space flight, immobilization, spinal cord injury, bed rest, and trauma. Examples of other conditions which result in disuse deconditioning include, for instance, simulated weightlessness, casting, and denervation.

Space flight, for example, alters many immune responses and regulatory components of the immune response, including the cytokine network. Space flight, as well as model systems of space flight, affect the production and activation of various cytokines including interleukins and TNF. Levels of IL-6 and IL-2 are elevated on the first day of space flight and again after returning from space flight.

Cytokines also modulate the function of osteoclasts, and IL-1 and TNF have been implicated in the rapid decalcification or loss of bone mineral density that results from immobilization, bed rest and spinal cord injury. Correlation between cytokine expression and increased retrograde transport following injury suggests that cytokines play a role in peripheral nerve damage. Bed rest, when combined with intra-articular administration of steroids, produces a particularly rapid systemic effect on the acute phase response that is mediated by cytokines.

A cytokine regulatory agent of the present invention or a composition containing the peptide can be used for treating disuse deconditioning by reducing or ameliorating the negative effects of disuse deconditioning associated with altered cytokine levels. The negative effects include, for example, loss of muscle mass, bone density, exercise capacity, and oxygen consumption as well as decreased levels of oxidative and antioxidant enzymes, such as soleus citrate synthase, in muscle tissue.

Organ Protection

Cytokines also play an important role in organ damage and organ protection. For example, cytokines significantly affect such events and conditions as organ transplant, particularly the rejection of a transplanted organ, transplant atherosclerosis, ischemia-reperfusion, cyclosporine-induced nephrotoxicity, myocardial infarction, and stroke.

Regarding organ transplant, cytokines, especially tumor necrosis factor (TNF), are important mediators of allograft rejection. Elevated serum levels of TNF occur in patients undergoing renal, hepatic, and cardiac allograft rejection. Further evidence of TNF presence has been demonstrated in rejecting rat cardiac and renal allografts as well as human renal and hepatic grafts. Acute rejection episodes in renal transplant patients are accompanied by an increase in serum IL-6 levels. The administration of glucocorticoids during such episodes was reported by Ray et al., *J. Am. Soc. Nephr.* 2(12):5214–5221 (1992), to lead to a rapid and marked decrease in IL-6 levels and the severity of the rejection episodes. The cytokine regulatory agents of the present invention can be similarly useful in reducing the severity of such rejection episodes and the damage caused thereby.

Administration of immunosuppressive agents, such as cyclosporine, to transplant subjects also effects cytokine activity, causing cyclosporine-induced nephrotoxicity resulting in damage to the kidney. Agents which regulate cytokines, such as those of the present invention, can be effective in reducing cyclosporine-induced nephrotoxicity.

In addition, cytokine regulatory agents of the present invention can protect against organ damage associated with ischemia-reperfusion, including such damage as decreased glomerular filtration rate and increased vascular resistance in the kidney. Ischemia-reperfusion injury has also been associated with elevations of cytokines. IL-1 and TNF mediate myocardial ischemia and increased levels of IL-1 can occur during the reperfusion phase of skeletal muscle ischemia. Increased TNF release follows both moderate and severe ischemic injury to the liver.

Thus, the present invention provides a method of protecting an organ of a subject against organ damage by administering a cytokine regulatory agent to the subject. The organ damage to be protected against can be the result of such conditions or events as an organ transplant, the administration of an immunosuppressive agent, such as cyclosporine, the resulting damage from ischemia-reperfusion, myocardial infarction, stroke, and the like.

As used herein "damage" includes damage to a whole organ, such as the dysfunctioning of an organ, or damage to a tissue of the organ. In many instances, such damage involves, not only increased cytokine levels, but also increases in free radicals. For example, the activated white blood cells that result from ischemia release oxygen radicals and deliver aggressive mediators such as cytokines and PAF, which are chemotactic for leukocytes. This results in a cycle in which oxygen radicals and mediators, such as cytokines, are responsible for the augmentation of post-ischemic damage.

The type of damage which free radicals or cytokines can induce includes, but is not limited to, inflammation, atherosclerosis, increases in vascular permeability, fibrosis, and necrosis. These and other types of damage can be assessed histomorphologically by methods well known in the art. Damage also can be evidenced by organ dysfunction that is often reflected by changes in physiological and biochemical parameters which tend to be specific to a particular organ or tissue and which can be routinely measured by techniques well known in the art. For example, kidney dysfunction, indicative of renal damage, might lead to decreases in glomerular filtration rate and renal blood flow as well as increased renal vascular resistance. Examples of biochemical parameters that can be used as early markers of tissue and organ damage include increased nitric oxide or malondialdehyde levels. Malondialdehyde is a byproduct of lipid peroxidation and, therefore, indicative of free radical levels. Alternatively, or in addition thereto, increased levels of such enzymes as lactate dehydrogenase, a marker of cell death, can be assessed.

Organs which can be protected against damage by administration of the cytokine regulatory agents of the present invention include, but are not limited to, the heart, kidney, liver, lung, brain, muscle, skin, or bone. An example of tissue within an organ which can be protected by the present invention is the epithelium in skin. Also included are organs which can be transplanted or which are associated with the negative side effects caused by the administration of an immunosuppressive agent to a transplant subject, as well as organs subject to ischemia-reperfusion, infarction, stroke, or other specific conditions or events which might lead to cellular damage or death. More than one organ may be protected at a time.

Cancer Chemotherapy

A cytokine regulatory agent of the present invention, or composition containing the agent, can also be used in cancer chemotherapy for reducing the nephrotoxic effect or other negative effects of cancer chemotherapeutic agents.

Cancer chemotherapeutic agents, such as cisplatin, Taxol® and Adriamycin®, induce and enhance the production of cytokines. Taxol®, a microtubule-stabilizing antineoplastic agent, induces expression of TNF and IL-1 and enhances the production of TNF in macrophages. Increased concentrations of IL-6 and TNF occur in patients receiving cisplatin, with cytokine concentrations being particularly elevated in patients experiencing renal or hepatic toxicity. Cytokine production is also increased in cancer patients during chemo-hyperthermia. TNF and IL-6 levels measured when a hyperthermia-inducing heating solution containing cisplatin was administered showed a dramatic increase in IL-6 occurring within 30 minutes after the treatment started. TNF values were only slightly elevated.

As shown in the Examples, use of a cytokine regulatory agent of the invention in cancer chemotherapy can reduce the nephrotoxic effect of a cancer chemotherapeutic agent. Moreover, the peptides can be administered to a subject undergoing cancer chemotherapy to reduce other negative side effects of chemotherapeutic drugs, including but not limited to, nausea, vomiting, mucositis, anorexia, fatigue, and other organ dysfunctions.

Diseases Mediated By Nitric Oxide and Cytokines, Including Diabetes and Glomerulonephritis Cytokines and nitric oxide (NO) are both important mediators of a variety of disease states, including, for example, diabetes and glomerulonephritis. Cytokines and NO regulate beta-cell damage in early insulin-dependent diabetes mellitus. IL-1, interferon gamma and TNF induce islet NO. In parallel with NO production, IL-1, interferon gamma, and TNF impair islet function, decrease glucose levels and decrease glucose-induced insulin release. Most of the deleterious effects caused by cytokines on islet cells can be prevented by blocking NO production. Although some studies have shown that isolated human islets are more resistant to the suppressive effects of cytokines and NO than isolated rodent islets, cytokines can suppress human islet function irrespective of their effects on NO generation.

Cytokines and NO also influence the degree of injury resulting from glomerulonephritis. TNF and IL-1 can increase the severity of glomerular injury in nephritis and, therefore, may be important in modulating glomerular injury clinically. Karker et al., *Clin. Expt. Immunol.* 90 (2):312–318 (1992), have reported that agents which suppress cytokines are effective in reducing elevated albumin levels and tissue damage in glomerulonephritis. Other research has demonstrated that in vivo induction of inducible nitric oxide synthase (iNOS) occurs in immune complex glomerulonephritis (Jansen et al., *Kid. Internat.* 45(4) :1215–1219 (1994)).

Cytokine regulatory agents of the present invention can be used for treating a subject having a disease mediated by nitric oxide and cytokines, such as diabetes and glomerulonephritis. As used herein, the term "treating" includes a meaning that encompasses reducing or alleviating one or more symptoms or conditions associated with a particular disease state mediated by NO and cytokines. For example, treating diabetes can be manifested by reducing glucose levels of a diabetic.

Effect of a Cytokine Regulatory Agent on Body Weight

Cytokine regulatory agents are useful for decreasing the body weight of a subject. In particular, the agents are useful for decreasing the weight of an obese subject. A link between obesity and non-insulin dependent diabetes mellitus (NIDDM) is well known in the art (see Hotamisligil and Spiegelman, *Diabetes* 43:1271–1278 (1994a)). Increased TNF-α expression has been detected in the adipose tissue of obese individuals and has been suggested as a having a role in the appearance of NIDDM in these individuals (Hotamisligil et al., *J. Clin. Invest.* 95:2409–2415 (1995)). However, efforts to neutralize TNF activity using an antibody that binds the TNF receptor did not result in significant weight loss when examined in a rat obesity/diabetes model, the Zucker fa/fa rat model (Hotamisligil et al., *J. Clin Invest.* 94:1543–1549 (1994b)).

Remarkably, administration of a cytokine regulatory agent, EX-2, to normal or obese rats resulted in a significant decrease in the rate of body weight gain or a significant decrease in body weight, depending on the dose administered (see Example XX). As used herein, the term "decrease in body weight" is used broadly to mean an actual decrease in body weight or a decrease in the rate of body weight gain over time, as compared to the normal weight gain expected in the period of time. As shown in Example XX, EX-2 also produced a small, but significant, decrease in the body weight of normal (non-obese) rats. These results indicate that a cytokine regulatory agent can cause a decrease in the rate of body weight gain and a decrease in body weight.

The weight loss observed in EX-2 treated rats correlated to an increased metabolic rate as determined by increased resting oxygen consumption. These result demonstrate that a cytokine regulatory agent also is useful for increasing the resting oxygen uptake of a subject. As discussed above, a cytokine regulatory agent also can attenuate the decrease of maximal oxygen consumption that occurs, for example, due to disuse deconditioning. The ability to increase maximal oxygen consumption in a subject can provide a significant clinical advantage to a subject suffering, for example, from congestive heart failure or other condition characterized by a deficiency in oxygen uptake such as the decrease in oxygen consumption that occurs during deconditioning (see Example XIII). Furthermore, the disuse deconditioning results demonstrate that repeated treatment with a cytokine regulatory agent for at least about two weeks can produce a positive adaptive change in a subject, resulting in increased aerobic capacity and exercise performance. Thus, a cytokine regulatory agent finds further use for increasing oxygen consumption in a subject. As used herein, the term "increasing oxygen consumption" or "increasing oxygen uptake" is used broadly to mean an increase above a normal baseline level of resting or maximal oxygen uptake by a subject or a decrease in the expected loss of resting or maximal oxygen consumption.

Treatment of Negative Side Effected Mediated by Cancer Chemotherapy in Humans Cytokine regulatory agents can be used to ameliorate or decrease the negative side effects of cancer therapeutic agents. A cytokine regulatory agent can be co-administered with a cancer therapeutic agents during a treatment regime for a cancer or can be co-administered in a prophylactic regime, for example, with Taxol®, which is administered to decrease the recurrence of breast cancer.

Example XIX discloses the use of the cytokine regulatory agent EX-2 to ameliorate the adverse side effects associated with cancer chemotherapeutic agents such as cisplatin, Taxol® and Adriamycin®, which induce and enhance the production of cytokines.

EX-2 can be administered by intravenous infusion to patients undergoing or about to undergo cancer chemotherapy or cancer chemopreventive regimes. For example, cisplatin, Taxol®, Adriamycin® or other chemotherapeutic or radiologic treatment can be co-administered with a cytokine regulatory agent in order to reduce or inhibit the adverse side effects caused by the chemotherapy or radiotherapy.

Increasing Levels of Cytokines in Mammals

A cytokine regulatory agent of the present invention, or composition containing the agent, can also be used to increase the physiologic level of one or more cytokines. For example, a particular condition can decrease the level or activity of a cytokine, which can inhibit all or part of an immune response or the immune system. Administration of a cytokine regulatory agent in a pharmacologically efficacious dose can enhance the level or activity of the cytokine, thereby permitting reducing the level of immunosuppression.

Figure 2:
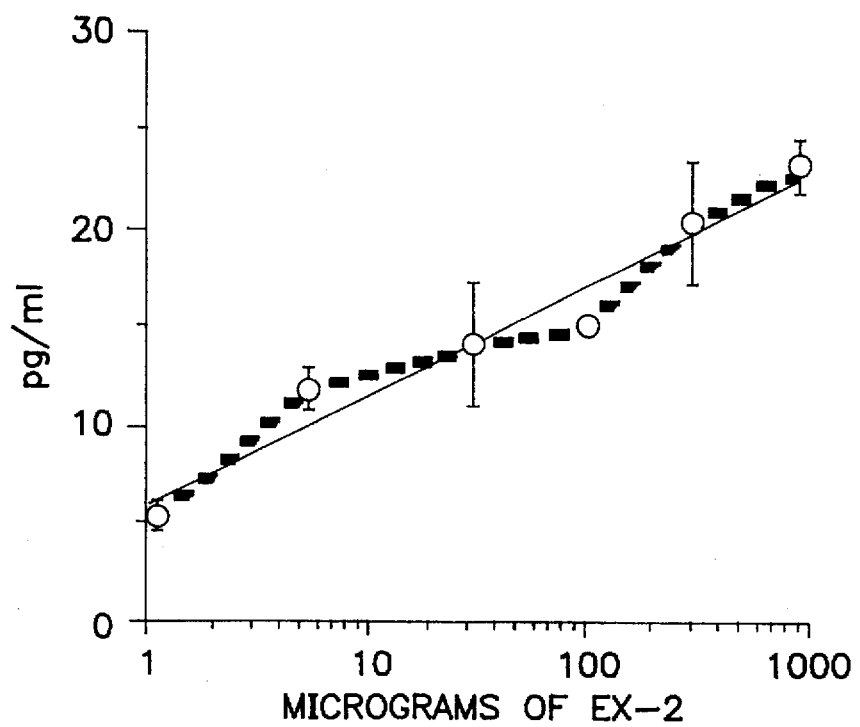
FIG. 2 demonstrates that EX-2 enhances IL-10 levels in mouse plasma.
Figure 3A:
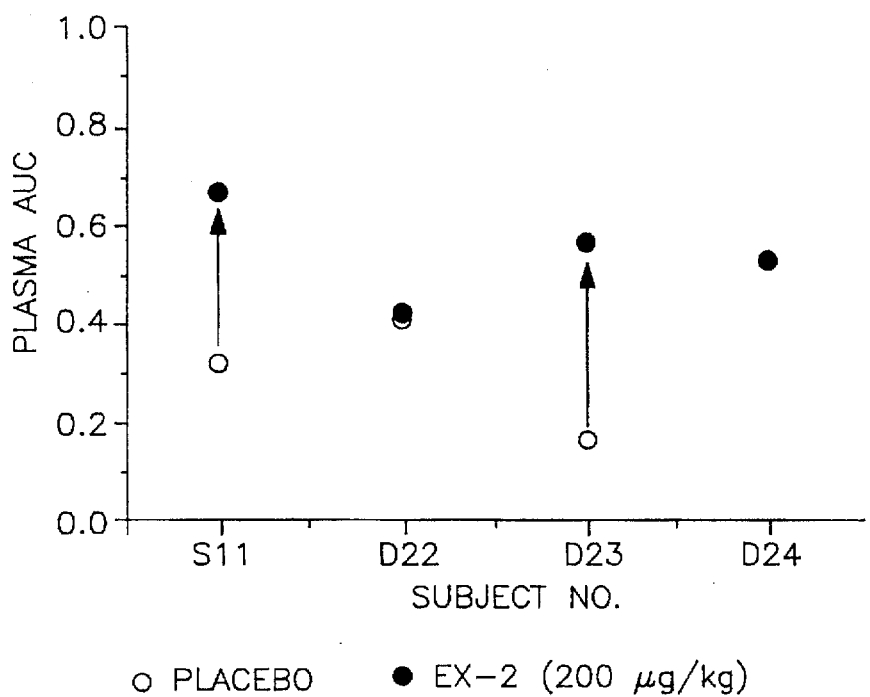
FIGS. 3a and 3b demonstrate that EX-2 induces IL-10 levels in human plasma.

A cytokine regulatory agent can increase the levels of IL-10 in a mammal such as a human (see FIGS. 2 and 3). IL-10 can block the activation of some inflammatory cytokines, including TNF, IL-1 and IL-6, while up-regulating cytokines such as IL-12. IL-10 also stimulates the proliferation of mast cells and thymocytes. IL-10 inhibits several monocyte and macrophage functions, including, for example, antigen presentation to T cells by depressing Class II MHC expression; synthesis of IL-1, IL-6, IL-8, CSF, and TNF; and microbicidal activities. The inhibited microbicidal activities include suppressing production of nitrogen oxides and bactericidal metabolites. As a consequence of monocyte and macrophage IL-10 mediated inhibition, activity of some types of helper T cells is inhibited. Particularly, the $T_H1$ cells, which are responsible for cell-mediated functions such as delayed-type hypersensitivity cells, and cytotoxic T cells are inhibited. As a further consequence $T_H1$ cell inhibition, activity of the $T_H2$ cells is augmented, particularly the T cell subset that augments B cell activation, bacterial and helminthic resistance and allergic reactions. As disclosed herein, administration of a cytokine regulatory agent can increase the plasma levels of IL-10 in mammals (see Example XVII and XVIII and FIGS. 2 and 3) and, therefore, can be useful for modulating, for example, immunoresponsiveness in a subject.

Cytokine regulatory agents or pharmaceutical compositions containing the peptides can be used for treating any of the above-described pathologies and conditions. One skilled in the art would know that a pharmaceutical composition comprising a cytokine regulatory agent can be administered to a subject having elevated cytokine activity by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis. Furthermore, the composition can be administered by injection, intubation, orally or topically, the latter of which can be passive, for example, by direct application of an ointment or powder, or active, for example, using a nasal spray or inhalant. A cytokine regulatory agent can also be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

Cytokines can be expressed locally, such as at a site of localized infection, or can be expressed systemically, for example, as in disuse deconditioning or in an immune response. Cytokine expression can induce pyrexia (fever) and hyperalgesia (extreme sensitivity to pain) in a subject, as well as macrophage and monocyte activation, which produces or further contributes to an inflammatory response in a subject. Since cytokine expression can be localized or systemic, one skilled in the art would select a particular route and method of administration of the cytokine regulatory agent based on the source and distribution of cytokines in a subject. For example, in a subject suffering from a systemic condition, such as disuse deconditioning, a pharmaceutical composition comprising a cytokine regulatory agent can be administered intravenously, orally or by another method that distributes the cytokine regulatory agent systemically. However, in a subject suffering from a pathology caused by localized cytokine expression, such as acute respiratory distress syndrome, a cytokine regulatory agent can be suspended or dissolved in the appropriate pharmaceutically acceptable carrier and administered directly into the lungs using, for example, a nasal spray.

In order to regulate the biological activity of a cytokine, the cytokine regulatory agent must be administered in an effective dose, which is about 0.0001 to 0.5 mg/kg body weight per injection, or by alternative modes of administration an effective dose is about 0.0001 to 100 mg/kg body weight. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a cytokine regulatory agent required to obtain an effective dose in a subject depends on many factors including the age and general health of the subject as well as the route of administration and the number of treatments to be administered. In view of these factors, the skilled artisan would adjust the particular dose so as to obtain an effective dose for efficaciously regulating cytokine activity.

Examples of cytokine regulatory agents and the effectiveness of a cytokine regulatory agent in preventing or minimizing or eliminating adverse biological effects mediated by cytokines are provided below and summarized in Tables I–V. As described below, cytokine regulatory agents such as the peptides described in Example II can effectively regulate cytokine expression in mice (Examples III and IV) and provide relief from cytokine-mediated pain, swelling, fever and lethality as demonstrated using mouse, rat and rabbit model systems that are recognized in the art as predictors of efficacy in humans (Examples V to XII).

The compounds described herein can be used as medicaments for the treatment of conditions such as inflammation, pain, cachexia and patho-immunogenic diseases such as arthritis, inflammatory bowel disease, systemic lupus erythematosus and other autoimmune dysfunctions, which are characterized by altered cytokine activity. In addition, the Examples provide evidence that a cytokine regulatory agent of the present invention is useful in attenuating the negative aspects of disuse deconditioning (Example XIII), protecting organs, particularly after ischemia-reperfusion injury and cyclosporine-induced nephrotoxicity (Example XIV), reducing the nephrotoxic effects of cancer chemotherapy (Example XV), treating disease states associated with nitric oxide, including diabetes and glomerulonephritis (Example XVI) and decreasing the body weight of an individual (Example XX).

Yet further evidence that the agents of the present invention regulate cytokine expression and, therefore, are useful in treating the above-mentioned conditions, is provided in Examples XVII to XVIX. Increasing cytokine levels in mammals, including mice (Example XVII) and humans (Example XVIII) subsequent to administration of a cytokine regulating agent provides additional evidence that the agents of the present invention regulate cytokine expression and activity.

The following examples are intended to illustrate, but not limit, the present invention.

EXAMPLE I

Synthesis of Peptide Cytokine Regulatory Agents

This example describes methods for the solid phase synthesis of peptide cytokine regulatory agents.

A. Nle-Gln-His-(D) Phe-Arg-(D) Trp-Gly-NH$_2$

A peptide cytokine regulatory agent having the amino acid sequence, Nle-Gln-His-(D) Phe-Arg-(D)Trp-GlY ("EX-1"), was synthesized using a modification of the solid phase peptide synthesis method of Merrifield (1964). Essentially, MBHA resin containing a t-BOC glycine derivative (Advanced Chemtech; Louisville, Ky.) was added to a reaction vessel suitable for solid phase peptide synthesis (see Houghten (1985), supra). The resin was washed three times with methylene chloride and the t-BOC protecting group was removed using trifluoroacetic acid (TFA) containing 1–2% anisole in methylene chloride. The resin then was washed with methylene chloride and treated with disopropylethylamine.

The peptide was extended by the addition of 3.2 equivalents of N-formyl-BOC-protected D-tryptophan in dimethylformamide and 3.0 equivalents of dicyclohexylcarbodiimide. The reaction was monitored using ninhydrin and was allowed to proceed for 25 min, after which the resin was washed using methylene chloride. The procedure was repeated using di-tolulyl-BOC arginine, then with each of the desired protected amino acids until the complete heptapeptide was synthesized.

Following synthesis of the heptapeptide, the N-formyl protecting group on the tryptophan residue was removed using 20% piperidine in DMF and the resin was washed with methylene chloride. The peptide was cleaved from the resin using anhydrous hydrogen fluoride (HF) containing 10% anisole, the reaction mixture was concentrated and the residue was extracted with aqueous acetic acid. The acetic acid fraction, which contained the dissolved sample, was removed and the residue was washed with water. The wash was added to the acetic acid fraction and the combined sample was concentrated. The resulting crude peptide was purified by RP-HPLC (Vydac, C-18 column, using a gradient of 1 to 60% solution B over 30 min (solution A is 0.1% TFA/water and solution B is 0.1% TFA/acetonitrile).

The peptide was determined to be 97% pure by RP-HPLC (Vydac C-18 column, using isocratic 24% solution B; solution A and solution B, as above; absorption determined at 215 nm). The mass of the purified heptapeptide was determined by plasma desorption mass spectrometry using a BioIon 20 Mass Analyzer time of flight detector. The mass of the EX-1 peptide was measured to be 942.7, which was essentially the same as the expected molecular mass (MS (M+1)=942.2).

B. His-(D) Phe-Arg-(D) Trp (CH$_2$)-(NAc) Gly-NH$_2$

A cytokine regulatory agent of the invention, having the amino acid sequence His-(D) Phe-Arg-(D)Trp(CH$_2$)-(NAc) Gly-NH$_2$, was synthesized and purified as described above, except for the following modifications. Boc-(D) Trp was converted to the corresponding N,O-dimethylhydroxamate using methyl chloroformate and N,O-dimethylhydroxyl amine hydrochloride. Reduction of the tryptophan amide with lithium aluminum hydride gave the Boc-(D)Trp aldehyde.

A solution of the Boc-(D)Trp aldehyde and sodium cyanoborohydride in DMF was added to glycine attached to the Rink amide resin in DMF containing 1% acetic acid. After the reductive amination was complete the secondary amine was acetylated with acetic anhydride and the resin was shaken with 1:1 trifluoroacetic acid and methylene chloride to remove the Boc group. Sequential coupling of the remaining amino acids was performed on an peptide synthesizer (Applied Biosystems) to produce the peptide His-(D)Phe-Arg-(D)Trp(CH$_2$)-(NAc) Gly-NH$_2$. The peptide was cleaved from the resin and purified as described above.

EXAMPLE II

Preparation of Acetylated Peptide Cytokine Regulatory Agents

This example describes methods for preparing N-acetylated peptide cytokine regulatory agents.

The heptapeptide Nle-Gln-His-(D) Phe-Arg-(D) Trp-Gly-NH$_2$ was synthesized as described in Example I.A., except that prior to cleaving the newly synthesized peptide from the resin, the amino terminus of the peptide was acetylated by treating the sample with acetic anhydride, diisopropylethylamine and methylene chloride for 2 hr. Following acetylation, the heptapeptide was cleaved from the resin, purified by RP-HPLC and characterized by mass spectrometry, as described above. The acetylated heptapeptide of Example II, designated, here, as EX-2, was determined to be 98% pure and the mass was measured to be 985.2 daltons, which was same as the expected molecular mass.

Similar methods as described in Examples I and II were used to synthesize other cytokine regulatory agents of the invention, including Ac-(cyclohexyl)Gly-Gln-His-(D) Phe-Arg- (D) Trp-Gly-NH$_2$ ("EX-3"); Ac- (D) Phe-Arg-(D) Trp-NH$_2$ ("EX-4"); Ac-His- (D) Phe-Arg- (D) Trp-Gly-NH$_2$ ("EX-5"); and Ac-His-(D)Phe-Arg-(D)TrP-NH$_2$ ("EX-6"). Ac-His-(D)Phe-Arg-(D) Trp(CH$_2$)-(NAc)Gly-NH$_2$ was prepared using the method described in Example I.B. except that, prior to cleaving the peptide from the resin, the peptide was acetylated using excess acetic anhydride.

EXAMPLE III

Reduction of Lipopolysaccharide-Induced Tumor Necrosis Factor Levels in Mice

This example describes the effectiveness of two cytokine regulatory agents for decreasing tumor necrosis factor (TNF) levels in lipopolysaccharide (LPS; endotoxin) treated mice.

Balb/c female mice weighing approximately 20 g were placed into two groups, a control group and a treated group. Five mg/kg of LPS in 0.9% saline was administered by intraperitoneal (IP) injection into the control mice. Mice in the treated group were first injected IP with 30 μg EX-2 or 150 μg EX-3 in saline, then, one min after EX-2 or EX-3 was administered, the mice received LPS as described for the control group.

Blood samples were collected from the orbital sinus of treated and control mice at various times up to four hr after LPS was administered. The plasma was separated by centrifugation at 3000×g for 5 min, then diluted with four volumes of 1× phosphate buffer saline (pH 7.4) containing 1% bovine serum albumin. A 100 μl sample of serum was assayed by ELISA for TNF-α (Genzyme; Cambridge Mass.).

The mean (+/− SEM) TNF-α level in six mice from each group was determined and the percent reduction in TNF levels was calculated. As shown in Table I, treatment of mice with EX-2 resulted in a 50% decrease in the level of TNF-α as compared to untreated control mice. Similarly, treatment of mice with EX-3 resulted in a 56% decrease in the level of TNF-α as compared to untreated control mice and treatment with EX-4 resulted in a 53% decrease (Table II). These results indicate that the peptides of the invention can restrain LPS-induced cytokine activity.

TABLE I

BIOLOGICAL DATA FOR CYTOKINE REGULATORY AGENT, EX-2

| Biological Test | Dose | Efficacy |
|---|---|---|
| Reduction in TNF levels | 30 µg/mouse | 50% |
| Reduction in IL-6 levels | 300 µg/mouse | 60% |
| Reduction in Carageenan-induced Paw Swelling | 1 µg/mouse | 45% |
| Inhibition of LPS-induced Lethality | 11 × 300 µg/mouse | 83% |
| Reduction in IL-1-induced Hyperalgesia | 1 µg/mouse | 125% |
| Reduction in LPS-induced PMN Count | 100 µg/kg | 58% |
| Reduction in IL-1-induced Fever | 500 µg/kg | 52% |
| Reduction in LPS-induced Fever | 50 µg/kg | 45% |
|  | 150 µg/kg | 52% |
| Reduction in arachidonic acid-induced Ear Swelling | 100 µg/mouse | 72% |
| Reduction in Morphine-induced Respiratory Depression | 10 + 20 + 20 µg/kg/rabbit | 50% |

TABLE II

BIOLOGICAL DATA FOR CYTOKINE REGULATORY AGENTS, EX-3 AND EX-4

| | | Efficacy | |
|---|---|---|---|
| Biological Test | Dose | EX-3 | EX-4 |
| Reduction in TNF levels | 150 µg/mouse | 56% | 53% |
| Reduction in Carageenan-induced Paw Swelling | 1 µg/mouse | 49% | NT |
| Inhibition of LPS-induced Lethality | 11 × 300 µg/mouse | 86% | 75% |
| Reduction in LPS-induced Fever | 150 µg/kg | 57% | 52% |
| Reduction in arachidonic acid-induced Ear Swelling | 100 µg/mouse | 62% | NT |
| Reduction in Morphine-induced Respiratory Depression | 10 + 20 + 20 µg/kg/rabbit | 65% | NT |

NT = not tested

EXAMPLE IV

Reduction of Lipopolysaccharide-Induced Interleukin-6 Levels in Mice

This example describes the effectiveness of a cytokine regulatory agent for decreasing Interleukin-6 (IL-6) levels in LPS treated mice.

Balb/c mice were grouped and treated as described in Example III, above. Blood samples were obtained from the orbital sinus at various times up to six hr and serum was collected and diluted as described above. A 100 µl aliquot was assayed for IL-6 levels using an IL-6-specific ELISA by a modification of the method of Starnes etal., *J. Immunol.* 145:4185–4194 (1990), which is incorporated herein by reference.

The mean (+/− SEM) IL-6 level in six mice from each group was determined and the percent reduction in IL-6 was calculated. As shown in Table I, treatment of mice with EX-2 resulted in a 60% decrease in the level of IL-6 as compared to untreated control mice.

EXAMPLE V

Carageenan-Induced Paw Swelling

This example describes the effectiveness of two cytokine regulatory agents for alleviating inflammation and pain.

Carageenan-induced paw swelling was induced using a modification of the methods of Hiltz and Lipton, *Peptides* 11:979–982 (1990); Vinegar et al., *Fed. Proc.* 46:118–126 (1987); and Vinegar et al., *J. Pharmacol. Expt. Therap.* 166:96–103 (1969), each of which is incorporated herein by reference. Briefly, adult female Balb/c mice were anesthetized by IP injection of 7 mg/kg ketoamine and 0.6 mg/kg rompun. Foot pad thickness was measured using a spring loaded micrometer (Swiss Precision Instruments). Foot pad thickness was expressed in units of 1/100 inch. After baseline measurements were obtained, mice were injected into a hind foot pad with either 0.2 ml physiologic saline (control) or varying doses of EX-2 or EX-3 in 0.2 ml saline (treated). The first injection was followed immediately by injection of 0.02 ml of 0.15% K-carageenan (Sigma Chemical Co.; St. Louis, Mo.).

Hind foot pad thickness was measured hourly for six hr, the change in thickness was determined and the percent reduction in swelling due to treatment with EX-2 was calculated. As shown in Tables I and II, IP injection of 1 µg EX-2 or 1 µg EX-3 reduced carageenan-induced swelling by 45% or 49%, respectively, when measured at the 2 hr time point.

EXAMPLE VI

Lipopolysaccharide-Induced Lethality

This example describes the effectiveness of the cytokine regulatory agents, EX-2, and EX-3 and EX-4, in reducing lethality from sepsis induced by administration of LPS.

These experiments were performed based on information reported by Rivier etal., *Endocrinology* 125:2800–2805 (1989), which is incorporated herein by reference. Adult female Balb/c mice were provided food and water ad libitum. Mice were injected IP every four hr for 40 hr with 30 to 300 µg EX-2, EX-3 or EX-4 in 0.2 ml saline (treated group) or with 0.2 ml saline, alone (control group) (10 mice per group). Immediately following the first injection, 0.6 mg LPS endotoxin in 0.2 ml saline was administered to each mouse. Following LPS injection, EX-2 or saline was administered to the treated mice or the control mice, respectively, every 4 hr for 36 hr.

As shown in Tables I and II, administration of 3.3 mg EX-2, EX-3, or EX-4 (11 injections of 300 µg each) produced an 83%, 86%, and 75%, respectively, increase in survival as compared to control mice. These results demonstrate that intraperitoneal administration of the cytokine regulatory agents of the invention can reduce lethality due to LPS-induced sepsis.

EXAMPLE VII

Reduction in Interleukin-1β-Induced Hyperalgesia

This example describes the effectiveness of a cytokine regulatory agent, EX-2, in providing pain prophylaxis.

These experiments were performed using a modification of the methods described by Poole etal., *Br. J. Pharmacol.* 106:489–492 (1992); Foilenfant et al., *Br. J. Pharmacol.* 98:41–43 (1989); and Randall and Sellito, *Arch. Internatl. Pharmacodyn.* 111:409–419 (1957), each of which is incorporated herein by reference. Adult male Sprague-Dawley rats (175–275 g) were tested for hyperalgesia by a paw pressure technique using variable pressure instrumentation (IITC Life Sciences; Woodland Hills, Calif.). Rats were acclimated to the housing environment and were handled for three days prior to beginning a training session. On the day before the hyperalgesia experiments was to begin, each rat was placed into a sock and two variable paw pressure tests were performed 15 min apart. The next day, the rats were pretested to determine the pressure (mm Hg) at which each animal exhibited escape reflexes such as whole body struggling and/or vocalization. Approximately 5–10% of the rats were non-responders and were eliminated from further experiments.

Animals that responded to the paw pressure were pretreated by IP injection of various concentrations of EX-2 in a volume of 1 ml/kg (treated) or saline, alone (control). After 20 min, 100 μl of IL-1β (1U/100 μl) was administered to rats via intra plantar injection. Two hr after IL-1 administration, rats were subjected to two additional paw pressure tests and the increase in mm Hg of pressure that could be applied to the EX-2-treated rats as compared to the control rats was determined. As shown in Table I, treatment with 1 μg EX-2 increased the amount of pressure the rats would tolerate by 125% as compared to the control rats.

EXAMPLE VIII

Adult Respiratory Distress Syndrome

This example describes the effectiveness of a cytokine regulatory agent, EX-2, in minimizing respiratory distress syndrome in LPS-treated rats.

These experiments were performed using a modification of the methods described by Ulich et al., *Am. J. Pathol.* 141:61–68 (1992) and by Wheelden et al., *Lab. Animals* 26:29–37 (1992), each of which is incorporated herein by reference. Male Harlan Sprague-Dawley rats were anesthetized using a mixture of 70 mg/kg ketamine and 6 mg/kg rompun injected IP. A 2–3 cm incision was made in the neck of each anesthetized rat and its trachea was exposed by blunt dissection of the surrounding soft tissue. The rats were suspended on a near vertical slab and intratracheal injections were performed by inserting into the exposed trachea, at a point 1 cm posterior to the larynx, a 25G×½ inch needle attached to a 1 cc syringe.

Each rat received 0.5 ml/kg of saline or 0.5 ml/kg of 10 mg/ml (5 mg/kg) LPS endotoxin via slow intratracheal administration. Immediately following administration of the LPS endotoxin, rats were injected IP with 1 ml/kg of either saline (control) or saline containing various concentrations of EX-2 (treated). The rats were maintained in the elevated position for 1–2 min to facilitate distribution of the LPS and saline into the lung. The incisions were closed and the rats were allowed to recover. Two and four hr post-intratracheal injection, saline or EX-2 again was administered IP to control and treated rats, respectively.

At 6 hr post-intratracheal injection, the rats were re-anesthetized and exsanguinated via cardiac puncture. Serum was collected and saved. The neck and chest were opened to expose the trachea and lungs, the lungs were lavaged with 6×5 ml saline using a 27G×¾ inch needle and the lavage fluid was pooled.

The total polymorphonuclear leukocytes (PMN; neutrophils) in the broncho-alveolar lavage fluid were counted in the EX-2-treated rats and compared with the number in the control rats. As shown in Table I, treatment with 100 μg/kg EX-2 inhibited the increase in PMN infiltration in LPS-treated lungs by 58%.

EXAMPLE IX

Inhibition of Interleukin-1β-or Lipopolysaccharide-Induced Temperature Increase This example describes the effectiveness of the cytokine regulatory agents, EX-2, EX-3 and EX-4, at inhibiting body temperature increase in rats in response to two different agents.

Male Wistar rats (45–75 days old) were placed in a temperature controlled room held at 26° C., which is thermoneutral for the normal body temperature of rats, and were maintained in the room with free access to food and water for 24 hr prior to testing. On the morning of the study, rats were marked for identification and weighed. The temperature of each rat was determined by placing the animal in a regulatory cage designed to minimize stress and inserting a temperature probe (YSI probe #402) 3–5 cm into the animal's rectum. The temperature was recorded 15 sec after the reading stabilized. Measurements were repeated 1 hr later to establish a baseline temperature for each rat.

After the baseline temperatures were established, rats were injected IP with saline, IL-1β or LPS endotoxin. Rats then were injected IP with either saline (control) or various concentrations of EX-2, EX-3, or EX-4 (treated). The temperature of the rats was measured every hr for 6 hr and the inhibition by EX-2, EX-3, or EX-4 of the rise in temperature due to IL-1β or LPS was determined.

As shown in Table I, treatment with 500 μg/kg EX-2 inhibited IL-1-induced fever by 52%. In addition, treatment with 50 or 150 μg/kg EX-2 inhibited LPS-induced fever by 45% or 52%, respectively, when measured 6 hr following LPS injection. Furthermore, treatment with 150 μg/kg EX-3 or EX-4 inhibited LPS-induced fever by 57% and 52%, respectively (Table II). These results demonstrate that various cytokine regulatory agents of the invention can effectively reduce fever.

EXAMPLE X

Reduction of Arachidonic Acid-Induced Ear Swelling in Mice

This example demonstrates that EX-2 and EX-3 can reduce arachidonic acid-induced ear swelling in mice.

Experiments were performed using female Balb/c mice weighing 18–23 grams. Saline or 100 μg EX-2 or EX-3 was administered IP, 30 min prior to topical application of arachidonic acid (AA). A 10 μl pipet was used to apply 10 μl AA solution (100 mg/ml ethanol; Calbiochem-Novabiochem; San Diego Calif.) to the inner and outer surfaces of the right ear of each mouse. Ten μl ethanol, alone, was applied to the inner and outer surface of the left ear of each mouse.

Ear thickness was measured with a hand-held spring loaded caliper immediately before and 60 min after AA application. Increase in ear thickness was calculated by subtracting the change observed in the control ear from the change observed in AA-treated ear. The value for each group (saline and control) is the average of the swelling observed in the individual mice in each group. The percent reduction of swelling is based on the swelling observed in the saline control group. As shown in Tables I and II, EX-2 and EX-3 reduced AA-induced ear swelling by 72% and 62%, respectively.

EXAMPLE XI

Reduction of Morphine-Induced Respiration Depression in Rabbits

This example demonstrates that EX-2 and EX-3 can reduce the depression in respiration induced by morphine in rabbits.

Male Shelton rabbits (3-4 kg) were restrained and fitted around the thorax, just behind the front limbs, with a respiration transducer (Model F-RCT; Grass Instruments; Quincy Ma). The transducer was connected to a grass polygraph via an EKG cable. An intravenous line was established for drug administration by cannulating the marginal ear vein using a 25 G butterfly needle.

Rabbit breathing was allowed to stabilize, then morphine sulfate (2 mg/kg in 0.5 ml saline) was administered by intravenous (iv) injection and respiratory rate and depth were monitored for 10 min. A second dose of morphine was administered, then, after 10 min, EX-2 or EX-3 (10 μg/kg in 0.5 ml saline) was administered, iv, and rabbits were monitored for 20 min. Two additional doses of EX-2 or EX-3 (20 μg/kg in 1.0 ml saline) were administered at 20 min intervals, i.e., 40 min and 60 min after the first morphine injection.

Results were calculated as the percent change from baseline values and are expressed as the difference of the mean value of the treated group minus the mean value of the control group at the end of the experiment (80 min). As shown in Tables I and II, EX-2 and EX-3 reduced the morphine-induced respiratory depression in rabbits by 50% and 65%, respectively.

EXAMPLE XII

Effect of Orally Administered Cytokine Regulatory Agents in Reducing TNF-α Levels and LPS-induced Lethality This example describes the oral effectiveness of various cytokine regulatory agents in reducing LPS-induced TNF-α levels and lethality in mice.

The LPS-induced lethality studies were performed based on information reported by Rivier et al., supra, 1989. Adult female Balb/c mice were provided food and water ad libitum. Mice were administered 150 μg or 300 μg EX-2, EX-3, EX-5 or EX-6 in 100 μl saline by gavage every 4 hr for 40 hr (total doses of 1.65 mg and 3.3 mg, respectively). Control mice received 100 μl saline, alone. Immediately following the first dose of cytokine regulatory agent or saline, 0.6 mg LPS in 0.2 ml saline was administered by IP injection. A statistically significant increase in survival was observed in mice receiving 3.3 mg EX-5 (63%), 1.65 mg EX-6 (68%) or 3.3 mg EX-5 (44%) as compared to control mice (0%) or mice receiving EX-2 or EX-3 (0% to 11%).

The ability of orally administered cytokine regulatory agents to reduce LPS-induced TNF-α levels also was examined. Balb/c female mice (20 g) were administered 150 μg or 300 μg EX-2, EX-3, EX-5 or EX-6 in 100 μl saline by gavage. Control mice received 100 μl saline, alone. One min later, 0.1 mg LPS was administered by IP injection. Samples were collected and TNF-α levels were determined as described in Example III, above.

The mean TNF-α levels in the mice from each group (n=9-20) was determined and the percent reduction in TNF-α levels was calculated. TNF-α levels were significantly reduced in mice receiving 150 μg EX-3 (49%); 300 μg EX-3 (40%) or 300 μg EX-5 (44%) as compared to control mice (0%) and mice receiving EX-2 (26% to 28%). These results demonstrate that various cytokine regulatory agents of the invention are effective when administered orally.

EXAMPLE XIII

Disuse Deconditioning in Rats

This experiment describes the effectiveness of a cytokine regulatory agent, EX-2, in ameliorating the negative effects associated with 14 days disuse deconditioning in rats.

Adult male Sprague-Dawley rats (355-365 g) were used in this study. Animals were housed individually in standard rat cages and were acclimated on a treadmill for 4 days. The next day, a baseline tail bleed was performed, followed by a maximal treadmill stress test the day after. The day following the stress test, the animals were divided into the appropriate treatment and control groups and the animals were suspended by their tails in suspension cages, which simulates weightlessness and, therefore, deconditions the animals. Another group of control animals was placed in standard rat cages with grated flooring similar to that utilized in the suspension cages. All animals were housed one per cage and supplied with food and water ad libitum. Body weights and food consumptions were measured daily. Animals received twice daily IP injections of 1 μg/kg or 5 μg/kg body weight of EX-2 (treated), or 1 ml/kg body weight of saline (control). On day 10, all animals were stress tested on the treadmill until they reached exhaustion. Data on maximum $VO_2$ and running time were collected and compared to pre-suspension results. On day 14, all animals were sacrificed, and blood, tissues, and organs were collected for further analysis. All procedures and tests were performed blind to avoid researcher subjectivity. Statistical significance ($p<0.05$) between groups was evaluated by ANOVA with Student-Newman-Keuls test for multiple comparisons. All data are reported as the mean ± standard error (SE).

Body weights decreased significantly for all suspended animals, regardless of treatment. Food consumption was not significantly different between the groups. All of the animals were subjected to the stress tests, which measured exercise time and maximal $VO_2$. As well, levels of the oxidative enzyme soleus citrate synthase and tibia bone density were measured.

As summarized in Table III, EX-2 exhibits a significant effect on many of the parameters associated with disuse deconditioning. Twice daily injections of low doses of EX-2 (1 or 5 μg/kg) significantly attenuated the deconditioning effects on exercise time, maximal $VO_2$, soleus citrate synthase levels, and tibia bone density. More specifically, EX-2 significantly attenuated both exercise performance parameters, exercise time and maximal $VO_2$, 44% and 80%, respectively, when compared to the decrease between the saline control and suspended animals. Soleus citrate synthase was attenuated by 50%. Tibia bone density measurements showed that EX-2 significantly attenuated suspension-induced bone demineralization by 50%. These results demonstrate that administration of a cytokine regulatory agent of the present invention reduces the negative effects of disuse deconditioning.

EXAMPLE XIV

Organ Protection

This example describes the effectiveness of a cytokine regulatory agent, EX-2, in preventing kidney

TABLE III

DISUSE DECONDITIONING

| Variable | % Attenuation * |
|---|---|
| Exercise Time | 44% ** |
| Maximal VO$_2$ | 80% ** |
| Soleus Citrate Synthase | 50% ** |
| Tibia Bone Density | 50% ** |

*-% attenuation of suspension-induced decrease of suspended groups as compared to control group.
**-significantly greater than suspended controls (p < 0.05).

damage in two rat models, an ischemia-reperfusion model and a cyclosporine-induced nephrotoxicity model.

A. Ischemia-Reperfusion Injury:

These experiments were performed to determine if a peptide which has cytokine regulatory properties, EX-2, can ameliorate the reperfusion-induced vasoconstriction and reduction in glomerular filtration rate that results from clamping of the renal artery. As a comparison, the NSAID ketorolac was utilized in the same model.

Sprague-Dawley rats (250–300 g) were anesthetized with inactin® (120 mg/kg). After deep anesthesia was assured, the rats were cannulated in the trachea with polyethylene (PE) tubing (PE 240), jugular vein, femoral artery, bladder (PE 50 for previous 3 cannulations), and left ureter (stretched PE 50). Once cannulation was completed, a 2 cm flank incision above the left kidney was performed and the renal pelvis and vascular bundle were exposed. The tissue surrounding the left renal artery was gently dissected away from the artery. The exposed renal artery was clamped for 1 hr using a small vascular cross-over clamp.

Just prior to clamping, EX-2 (50 or 500 µg/kg), ketorolac (KETO, 1 mg/kg), or vehicle was administered intravenously (iv) After 1 hr of clamping (ischemia), the clamp was gently removed with care taken to avoid damaging either the renal artery or nerves. An infusion of $^3$H-Inulin (NEN/Dupont; Wilmington, Del.), (0.6 µCi/ml in phosphate buffered saline (PBS) (2 ml/hr) was initiated at a constant rate of 4 µCi/hr. After 60 min of reperfusion, glomerular filtration rate (GFR), renal plasma flow (RPF) and renal vascular resistance (RVR) were assessed in two 30 min collection periods. The kidney was then removed for analysis. Sham operated and clamped rats served as controls for the above group. Contralateral renal function was utilized to determine the stability of the rat's renal function during the measured period. The results demonstrate that EX-2 effects an increase in glomerular filtration rate and decrease in vascular resistance (Table IV). This data provides that a present cytokine regulatory agent effectively protects the kidney against damage associated with ischemia-reperfusion.

B. Cyclosporine-induced Nephrotoxicity:

This experiment was performed to ascertain if EX-2 can mitigate the reduction in glomerular filtration rate (GFR) and renal blood flow, as well as the

TABLE IV

RENAL ISCHEMIA/REPERFUSION (I/R)

| | GFR | RVR (ml/mm) | RPF |
|---|---|---|---|
| Sham | 1.0 ± 0.1 | 1.0 ± 0.1 | 4.2 ± 0.4 |
| I/R + PBS | 0.2 ± 0.1 | 6.6 ± 2.1 | 0.8 ± 0.2 |
| I/R + EX-2 | 0.5 ± 0.1 | 1.8 ± 0.2 | 2.3 ± 0.3 | dysfunction in fluid and electrolyte homeostasis induced by immunosuppressive treatment with cyclosporine A.

In the first study, male Sprague-Dawley rats (n=43) with a weight range of 240–290 g at the initiation of the cyclosporine A (CsA) treatment were divided into 4 weight matched groups. The groups were as follows: (1) Control: no CsA, no EX-2, treatment only with CsA vehicle (PBS) PO and EX-2 vehicle (also PBS) IP; (2) CsA: treatment with CsA (50 mg/kg in PBS administered PO daily at 0830 hr for 9 days) and IP injections of PBS (Ex-2 vehicle); (3) CsA and 50 µg: CsA treatment identical to group 2 with the addition of EX-2 (50 µg/kg IP administered daily at 0800 and 1700 hr in EX-2 vehicle); and (4) CsA and 500 µg: CsA treatment identical to groups 2 and 3, and EX-2 treatment protocol similar to group 3 except that the dose of EX-2 was 500 µg/kg BW. After deep anesthesia was assured, the rats were cannulated in the trachea (PE 240) jugular vein, femoral artery, and bladder (PE 50 for the previous 3 cannulations). After cannulation, infusion of $^3$H-inulin was initiated 50 min prior to the measurement period to assess glomerular filtration rate, renal blood flow and plasma flow. Renal blood flow was determined by the inulin extraction technique. At the end of the study, the kidneys were removed for histological analysis.

In the second study, male Sprague-Dawley rats (n=31) with a weight range of 240–290 g at the time of initiation of the cyclosporine treatment were divided into 4 weight-matched groups. The time course and protocol of this study matched the first study with the following exceptions: (1) The daily dose of CsA was reduced to 30 mg/kg and was administered subcutaneously (SC) and (2) the 50 µ/kg dose of EX-2 was substituted with a twice daily dose of 200 µg/kg. The 500 µg/kg dose of EX-2 was repeated in this study. Renal hemodynamics were determined and extracellular fluid volumes were also assessed.

CsA treatment did not significantly decrease renal blood flow in these studies due to the scatter in the data. However, EX-2 treatment improved blood flow to values not different from control. In the second study, where extracellular fluid volumes (ECF) were measured, there were no differences in ECF among control and treatment groups (27.6±1.9 in control, 27.5±1.7 in CsA and vehicle, 26.2±0.9 in CsA +200 µg/kg EX-2, and 25.7±1.4% in CsA +500 µg/kg EX-2).

Figure 1B:
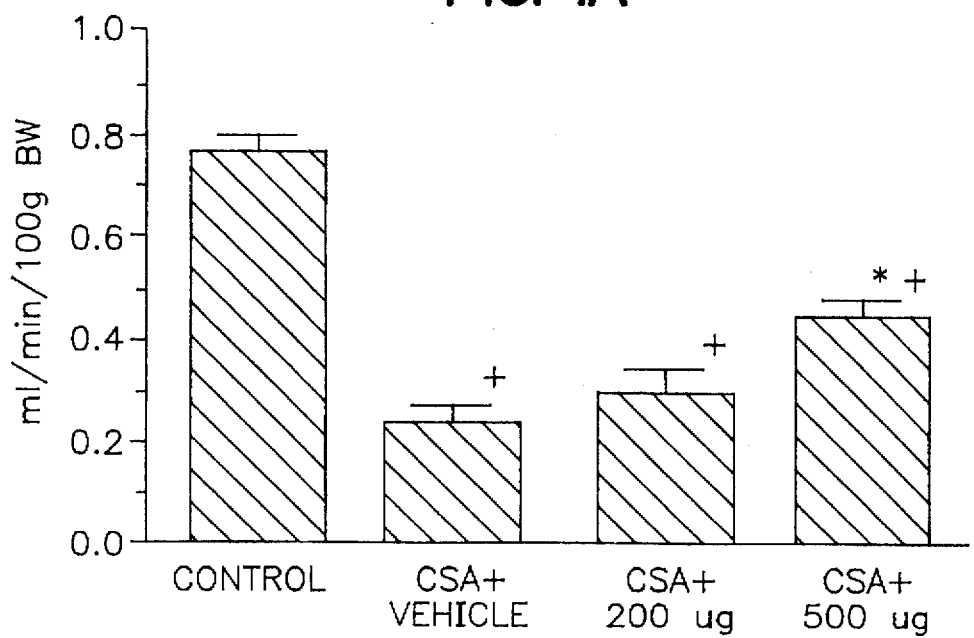

Urinary protein excretion was also measured and the data demonstrated that EX-2 treatment did not increase urinary protein excretion compared to CsA-treated rats despite the significant increase in GFR. EX-2 significantly increased GFR, compared to CsA and vehicle controls, in both studies and returned renal blood flow to values not different from control. There were no changes in ECF as a result of EX-2 treatment and there was a trend to decreased urinary protein excretion normalized to glomerular filtration rate. The results from the two experiments are shown in FIGS. 1a and 1b and provide evidence that a cytokine regulatory agent of the present invention reduces cyclosporine-induced nephrotoxicity and the damage caused thereby.

EXAMPLE XV

Cancer Chemotherapy

This example describes the effectiveness of a cytokine regulatory agent, EX-2, in reducing the nephrotoxic effects of cancer chemotherapeutic agents.

Male Sprague-Dawley were used to determine the effect of EX-2 on renal function after cisplatin (CDDP) administration. All rats were administered CDDP (4 mg/kg IP) and divided in 3 treatment groups (n=6/group). The groups were as follows: (1) Administration with vehicle and sterile PBS 3x/day; (2) Administration of EX-2 at a dose of 5 µg/kg, 3×/day; and (3) same as group 2 except the dose of EX-2 was 50 µg/kg, 3×/day.

An infusion of $^3$H-inulin (0.6 µCi/ml in PBS) (2 ml/hr) was initiated at the end of the surgical preparation period. The continuous infusion was started 60 min prior to the renal function measurements and maintained to the end of the study. Glomerular filtration was assessed by inulin clearance techniques in two 30 min periods and renal blood flow (RBF) and renal plasma flow (RPF) were measured by inulin extraction techniques (arterial vs. renal vein inulin concentration) from left kidney renal vein blood sampled at the end of the second GFR measurement period. Urinary output was also monitored to determine both urine flow and fractional excretion of water. Urinary electrolyte ($Na^+$ and $K^+$) concentrations were analyzed by flame photometry (Model 51 Ca, Bacharch, inc.; Pittsburgh, Pa.) and urinary protein concentrations were determined. At the end of the measurement periods, the kidneys were removed for histological analysis. The influence of varying treatment doses of EX-2 on renal function in 3 CDDP administered rats (CDDP at 4 mg/kg IP) is summarized in Table V. The data demonstrates that a cytokine regulatory agent of the present invention increases glomerular filtration rate, renal plasma flow and renal blood flow, thereby reducing the nephrotoxicity of a cancer chemotherapeutic agent.

TABLE V

CANCER CHEMOTHERAPY

|  | GFR | RPF (ml/mm) | RBF |
|---|---|---|---|
| CDDP + vehicle | 1.0 ± 0.4 | 5.6 ± 0.9 | 10.2 ± 1.6 |
| CDDP + 5 µg/kg | 0.8 ± 0.2 | 6.5 ± 1.0 | 12.1 ± 2.0 |
| CDDP + 50 µg/kg | 1.6 ± 0.4 | 8.8 ± 1.1 | 16.8 ± 2.2 |

EXAMPLE XVI

Treatment of Diseases Mediated by Nitric Oxide and Cytokines

This example describes the effectiveness of EX-2 at inhibiting inducible nitric oxide synthase (iNOS) and decreasing glucose in streptozotozin-induced diabetes and in reducing albumin levels in glomerulonephritis.

A. Inducible Nitric oxide Synthase (iNOS):

Rat aorta smooth muscle cells (RASMC) were isolated from male rats (325–350 g) using the previously published procedures of Gelsterfer et al., Circ. Res. 62:749–756 (1988), which is incorporated herein by reference. Cells were positively identified as smooth muscle cells by indirect immunofluorescent staining for anti-α-actin, using a mouse anti-α-actin antibody and anti-mouse IgG FITC conjugate. Cells were grown in T-75 tissue culture flasks (Corning Delbelco's Glass, Inc.; Corning, NY) in 50% F12 and 50% Delbelco's Modified Eagle Medium (DMEM) supplemented with 10% bovine serum, 0.2 g/1 L-glutamine, penicillin (100 U/ml) and streptomycin (0.1 mg/ml).

Cells between passages 1–5 were pretreated with one of the following: vehicle, LPS (1 µg/ml), IL-1β (10 U/ml), or TNF-α (100 U/ml) for 6 hr. In similar groups, 0.1 or 1 µM of EX-2 was added 10 min before the addition of LPS, IL-1β or TNF-α. Six hr later, cells were washed with Earle's balanced salt solution and incubated for 30 min with vehicle of 100 µM L-nitro arginine methyl ester (L-NAME). Accumulation of cGMP was determined following exposure to 0.3 mM 3-isobutyl-1-methyl xanthine (IBMX in the presence or absence of 1 mM L-arginine. Medium was then rapidly aspirated and 500 µl of 0.1N HCl was added to each well to stop the reactions and extract cGMP. Thirty min later, the $HC_1$ extract was collected and cell remnants removed from the wells by adding hot 1.0N NaOH and scraping the well with a rubber policeman. The HCl extract was analyzed for cGMP by RIA and the NaOH-solubilized cell remnants were used for protein determination.

Male Sprague-Dawley rats were anesthetized with 55 mg/kg pentobarbital IP. Catheters were inserted into the carotid artery and jugular vein for blood withdrawal and drug administration, respectively. EX-2 or saline was given to a group of 6 rats. One hr later, while rats were still under anesthesia, blood was withdrawn into a heparinized syringe and plasma was obtained by centrifugation. RASMC were incubated with plasma from control or EX-2-treated animals and the ability of plasma components to inhibit the induction of INOS by LPS or IL-1β was determined as above.

The radioligand ($^{125}$I-succinyl cGMP-tyrosine methyl ester) was prepared by the method of Hunter and Greenwood Nature, 94:495–496 (1962), which is incorporated herein by reference, using carrier free $^{125}$I. The iodination reaction products were separated by RP-HPLC following the procedures of Patel and Lindent, Anal. Biochem. 168:417–425 (1988), which is incorporated herein by reference. Using a monoclonal antibody for cGMP, RIA was performed in the Gammaflow™ automated RIA system as disclosed in Brooker et al., Science 191:270–276 (1976), which is incorporated herein by reference. Standard stock solutions of cGMP (20 µM) were prepared in 0.1N HCl and the absorbance of the solution was routinely monitored spectrophotometrically (Shimadzu, UV 16OU). Standard dilutions (0.63–80 nM) were made from stock solution. The HCl extract containing cGMP was used for RIA directly. Results are summarized in Table V below and demonstrate that EX-2 can inhibit inducible nitric oxide synthase, thereby reducing levels of NO production and the negative effects associated therewith, such as diabetes or glomerulonephritis.

B. Induced Diabetes:

Male Sprague-Dawley rats were given 65 mg/kg of streptozotocin (STZ) intravenously through the tail vein. Rats were divided into two groups. The first group was administered EX-2, 150 µg/kg every 8 hr for 72 hr and the second group was a control. Blood samples were withdrawn under ether anesthesia every 8 hr for the first 72 hr, then every 12 hr or 24 hr until the end of the observation period. Plasma samples were assayed for glucose using a glucose assay kit (Trinder, Sigma Chemical Co.). As shown in Table VI below EX-2 effect a 72% reduction in blood glucose levels.

C. Heritable Diabetes:

Male Zucker rats are a well established rat model for heritable non-insulin dependent diabetes mellitus (NIDDM), as described, for example, by Ward et al., Ann. Clin. Lab. Sci., 24:266–277, (1994), which is incorporated herein by reference. Eighteen male Zucker rats were used to study the effects of EX-2 on NIDDM, a chronic disease. The rats were placed into two groups and received either saline or 25 µg/kg EX-2 every 8 hr for approximately three months. Blood samples were collected by tail clip and urine samples were collected by placing animals in metabolic cages fro 24 hr. Plasma insulin was assayed using an RIA kit (Amersham Life Sciences, Arlington Heights, Ill.). Urine protein was assayed for using a commercial protein assay kit (Coomassie Plus, Pierce, Rockford, Ill.). Body weighed measurements were made with a Mettler Toledo top loader balance. As shown in Table VI, EX-2 effected a 39% reduction in insulin, a 87% reduction in urine protein, and approximately 100 gram decrease in body weight reduction; see Example XX).

TABLE VI

DIABETES AND GLOMERULONEPHRITIS

| Model/Assay | Measure | % Reduction * |
|---|---|---|
| iNOS | cGMP (pmol/100 mg/15 min) | 60% |
| STZ Diabetes | Blood Glucose (mg/dl) | 72% |
| Zucker NIDDM Diabetes | Insulin (ng/ml) | 39% |
|  | Urine Protein (mg/24 hr) | 87% |
|  | Body Weight (grams) | 32% |
| Glomerulonephritis | Urine Albumin (mg/day) | 62% |

* Percent reduction of increases in measures that were induced by Model/Assay by administration of EX-2.

D. Glomerulonephritis:

Male Sprague-Dawley rats (weight 194–248 g) were immunized by subcutaneous injection of 1 mg normal rabbit IgG (Sigma Chemical Co.) in Freund's complete adjuvant (Sigma Chemical Co.). EX-2 was administered 3 times per day (100 µg/kg per injection) throughout the duration of the experiment. Seven days later, the rats were injected with 1.5 ml of nephrotoxic serum iv via dorsal penile vein. Urine, plasma, and serum were collected before injection of nephrotoxic serum at 4, 6, 24, 48, and 96 hr thereafter. All rats developed acute glomerulonephritis with albuminuria that increased progressively from 4 to 96 hr, as demonstrated by 24 hr albumin excretion. Albuminuria was quantified by immunoelectrophoresis. The results are summarized below in Table VI and show that a cytokine regulatory agent of the present invention attenuates the increase in albumin levels seen in glomeruleronephritis, which is an indication of improvement in the disease state.

In summary, the above data demonstrate that a cytokine regulatory agent of the present invention inhibits inducible nitric oxide synthase levels, thereby reducing the production of NO. The cytokine regulatory agents are also useful for treating particular diseases in which nitric oxide contributes to tissue damage such as diabetes, glomerulonephritis, atherosclerosis and multiple sclerosis.

EXAMPLE XVII

Increasing Levels of IL-10 in Mice

This example describes the effectiveness of EX-2 In increasing the levels of IL-10 in mammals using the increase in mouse plasma subsequent to EX-2 administration as an illustrative example.

FIG. 2 shows the IL-10 inducing effect of EX-2, also designated, in mouse plasma. EX-2 was administered intraperitoneally to 19 mice in doses ranging from 1.0 ug/mouse to 1000.0 ug/mouse. Results showed a dose dependent increase in IL-10 levels ranging from 5.0 pg/ml to 23.0 pg/ml.

EXAMPLE XVIII

Increasing Levels of IL-10 in Humans

This example shows the cytokine enhancing effect of the cytokine regulatory agent EX-2 in a human subject.

Figure 3B:
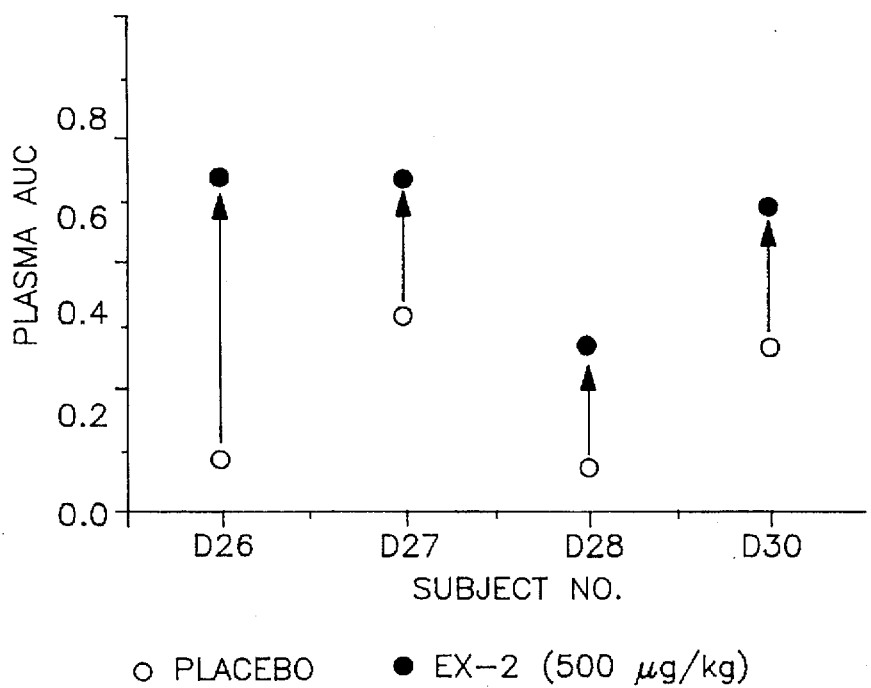

EX-2 was administered by intravenous infusion to eight healthy male volunteers in doses of either 200 or 500 ug/kg. Plasma IL-10 levels increased in two of four volunteers after administration at 200 ug/kg EX-2 (FIG. 3a) and in four of four volunteers after administration of 500 ug/kg EX-2 (FIG. 3b). The results show an 85% increase of IL-10 in subjects receiving 200 ug/kg EX-2 and an increase of 230% in subjects receiving 500 ug/kg EX-2.

EXAMPLE XIX

Treatment of the Adverse Side Effects Caused by Cancer Chemotherapy in Humans

This example describes the utility of a cytokine regulatory agent such as EX-2 in ameliorating the adverse side effects associated with the cancer chemotherapy using cisplatin, Taxol® or Adriamycin®, which induce and enhance the production of cytokines.

EX-2, for example, can be administered by IV infusion to patients undergoing or about to undergo chemotherapy. For example, a patient can be scheduled to receive cisplatin, Taxol®, Adriamycin® or another appropriate chemotherapeutic or radiologic treatment. EX-2 can be administered in a dose of about between 1 and 1000 ug/kg, with a preferred infusion dose of 500 ug/kg. Doses can be administered by continuous drip or by intermittent bolus.

EXAMPLE XX

Reduction in Body Weight Due to Administration of a Cytokine Regulatory Agent

This example demonstrates that administration of a cytokine regulatory agent can cause a decrease in the body weight of a subject.

Adult Zucker fatty rats (fa/fa; 325–350 g) or non-obese Zucker rats (Fa/+; 250–275 g) each were divided into two groups. One group each of fa/fa and Fa/+ rats received intraperitoneal (ip) injections of 250 µg/kg EX-2, 3×/day, for 86 days, followed by 2×/day treatments for an additional 29 days. The other group of fa/fa and Fa/+rats received saline on the same schedule.

Figure 4:
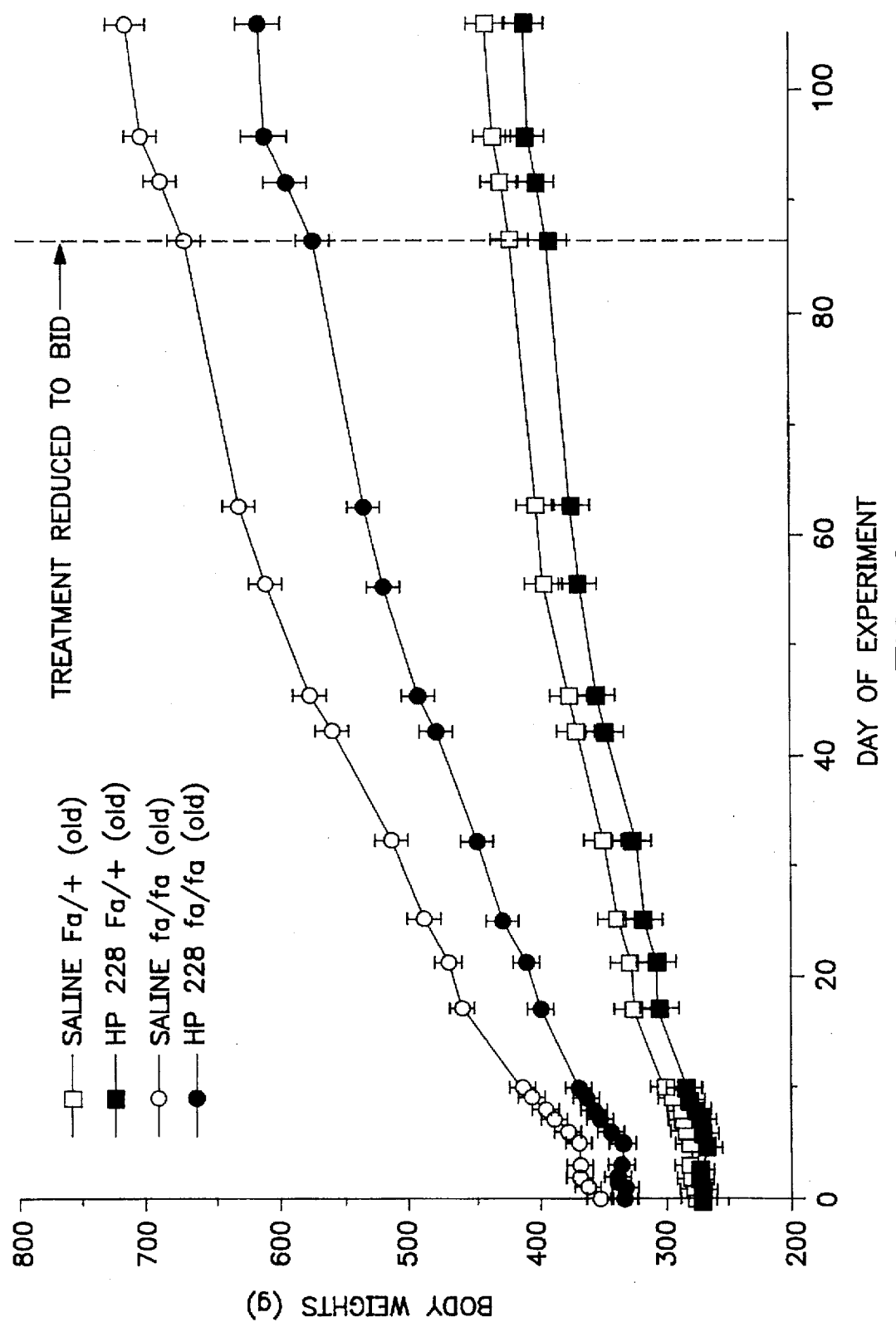
FIG. 4 shows the body weights of obese (fa/fa) and normal (Fa/+) rats treated with EX-2.

Administration of EX-2 caused a significant decrease in the weight gain of fa/fa and of Fa/+ rats (see FIG. 4). Specifically, saline treated fa/fa rats gained about 360 g during the 105 day treatment, whereas EX-2 treated fa/fa rats only gained 275 g, representing a 24% decrease in weight gain. Significantly, this decrease in weight correlated to decreased epididymal fat pad weight, indicating that fat, not lean muscle mass, weight is decreased by administration of EX-2. In Fa/+ rats, the decreased weight gain was more modest, but again correlated to fat mass rather than lean muscle mass. These results indicate that a cytokine regulatory agent can decrease weight gain in normal and obese subjects by decreasing the accumulation of fat.

In other experiments, fa/fa rats received 0.5–10 mg/kg EX-2, 2×/day, for 14 days (1–20 mg/day). A decreased rate of weight gain was observed in each group. Furthermore, rats treated with 20 mg EX-2/day showed about a 10% decrease in body weight. This weight loss correlated with increased consumption by the EX-2 treated rats as compared to the controls. These results indicate that a cytokine regulatory agent is useful for decreasing the body weight of a subject.

Although the invention has been described with reference to the examples provided above, it should be understood that various modifications can be made by those skilled in the art without departing from the invention. Accordingly, the invention is set out in the following claims.

We claim:

1. A method of enhancing cytokine activity in a subject having a condition characterized by altered or aberrant cytokine activity, comprising administering to the subject an effective amount of a cytokine regulatory agent, comprising $X_1$-$X_2$-His-(D)Phe-Arg-(D)Trp-$X_3$,
wherein
$X_1$ is

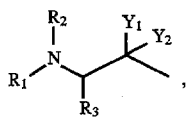

H or $COCH_3$;
$X_2$ is

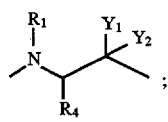

and
$X_3$ is

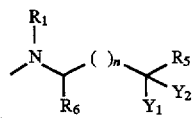

or $R_5$;
wherein $Y_1$ and $Y_2$ are independently a hydrogen atom, or are taken together to form a carbonyl or thiocarbonyl; $R_1$ is H, $COCH_3$, $C_2H_5$, $CH_2Ph$, $COPh$, $COOCH_2Ph$, $COO$-t-butyl, $CH_2CO$-(polyethylene glycol) or A; $R_2$ is H or $COCH_3$; $R_3$ is a linear or branched alkyl group having 1 to 6 carbon atoms or a cyclic alkyl group having 3 to 6 carbon atoms; $R_4$ is $(CH_2)_m$-$CONH_2$, $(CH_2)_m$-$CONHR_1$ or $(CH_2)_m$-$CONHA$; $R_5$ is OH, $OR_3$, $NH_2$, SH, $NHCH_3$, $NHCH_2Ph$ or A; and $R_6$ is H or $R_3$:

and wherein "Ph" is $C_6H_5$, "m" is 1, 2 or 3, "n" is 0, 1, 2 or 3, and "A" is a carbohydrate having the general formula:

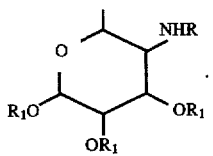

2. The method of claim 1, wherein said cytokine activity is IL-10 activity.

3. The method of claim 1, wherein said condition is an inflammatory response.

4. The method of claim 1, wherein said condition is cachexia.

5. The method of claim 1, wherein said condition is a patho-immunogenic response.

6. The method of claim 1, wherein said condition is adult respiratory distress syndrome.

7. The method of claim 1 or 17, wherein the amino terminus of the cytokine regulatory agent is modified.

8. The method of claim 7, wherein the amino terminus is modified by acetylation.

9. The method of claim 1 or 17, wherein the carboxyl terminus of the cytokine regulatory agent is modified.

10. The method of claim 9, wherein the carboxyl terminus is modified by amidation.

11. The method of claim 1 or 17, wherein $R_1$ is selected from the group consisting of H, $C_2H_5$ and $CH_2Ph$.

12. The method of claim 1 or 17, wherein $R_1$ and $R_2$ are each H.

13. The method of claim 1, wherein $X_1$ is selected from the group consisting of norleucine, norvaline, leucine and isoleucine.

14. The method of claim 1, wherein $R_5$ is covalently bound to $X_1$, the covalent bond forming a cyclic peptide.

15. A method of decreasing the body weight of a subject, comprising administering to the subject an effective amount of a cytokine regulatory agent, comprising
$X_1$-$X_2$-His-(D) Phe-Arg-(D) Trp-$X_3$,
wherein
$X_1$ is

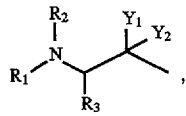

H or $COCH_3$;
$X_2$ is

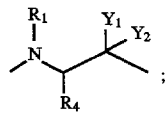

and
$X_3$ is

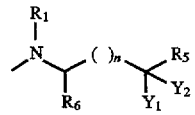

or $R_5$;
wherein $Y_1$ and $Y_2$ are independently a hydrogen atom, or are taken together to form a carbonyl or thiocarbonyl; $R_1$ is H, $COCH_3$, $C_2H_5$, $CH_2Ph$, $COPh$, COO-t-butyl, $CH_2CO$-(polyethylene glycol) or A: $R_2$ is H or $COCH_3$; $R_3$ is a linear or branched alkyl group having 1 to 6 carbon atoms or a cyclic alkyl group having 3 to 6 carbon atoms; $R_4$ is $(CH_2)_m$-$CONH_2$, $(CH_2)_m$-$CONHR_1$ or $(CH_2)_m$-$CONHA$; $R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula;

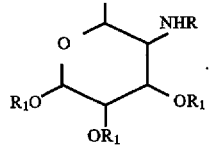

16. A method of increasing the oxygen consumption of a subject, comprising administering to the subject an effective amount of a cytokine regulatory agent, comprising $X_1$-$X_2$-His-(D)Phe-Arg-(D)Trp-$X_3$, wherein $X_1$ is

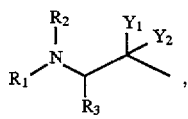

H or $COCH_3$;

$X_2$ is

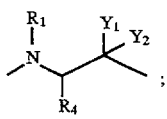

and $X_3$ is

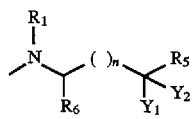

or $R_5$;

wherein $Y_1$ and $Y_2$ are independently a hydrogen atom, or are taken together to form a carbonyl or thiocarbonyl;

$R_1$ is H, $COCH_3$, $C_2P_5$, $CH_2Ph$, $COPh$, $COOCH_2Ph$, COO-t-butyl, $CH_2CO$-(poiyethylene glycol) or A:

$R_2$ is H or $COCH_3$;

$R_3$ is a linear or branched alkyl group having 1 to 6 carbon atoms or a cyclic alkyl group having 3 to 6 carbon atoms;

$R_4$ is $(CH_2)_m$-$CONH_2$, $(CH_2)_m$-$CONHR_1$ or $(CH_2)_m$-CONHA;

$R_5$ is OH, $OR_3$, $NH_2$, SH, $NHCH_3$, $NHCH_2PH$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

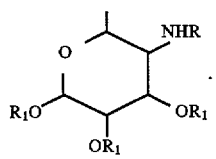

17. A method of enhancing cytokine activity in a subject having a condition characterized by altered or aberrant cytokine activity, comprising administering to the subject an effective amount of a cytokine regulatory agent, comprising $X_4$-$X_5$-(D) Phe-Arg-(D)Trp-$X_3$, wherein $X_4$ is

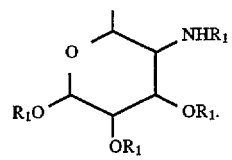

H, $COCH_3$, or absent;

$X_5$ is His, H, or $COCH_3$; and $X_3$ is

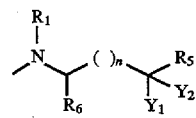

or $R_5$;

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, $COPh$, $COOCH_2Ph$, COO-t-butyl, $CH_2CO$-(polyethylene glycol) or A:

$R_2$ is H or $COCH_3$;

$R_3$ is a linear or branched alkyl group having 1 to 6 carbon atoms or a cyclic alkyl group having 3 to 6 carbon atoms;

$R_4$ is $(CH_2)_m$-$CONH_2$, $(CH_2)_m$-$CONHR_1$ or$(CH_2)_m$-CONHA;

$R_5$ is OH, $OR_3$, $NH_2$, SH, $NHCH_3$, $NHCH_2Ph$ or A: and $R_6$ is H or $R_3$;

and wherein "Ph" is $C_6H_5$, "m" is, 1, 2 or 3, "n" is 0, 1, 2, or 3, and "A" is a carbohydrate having the general formula:

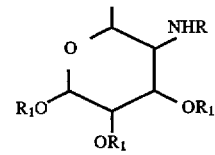

18. The method of claim 17, wherein said cytokine activity is IL-10 activity.

19. The method of claim 17, wherein said condition is an inflammatory response.

20. The method of claim 17, wherein said condition is cachexia.

21. The method of claim 17, wherein said condition is a patho-immunogenic disease.

22. The method of claim 17, wherein said condition is adult respiratory distress syndrome.

23. The method of claim 17, wherein $R_5$ is covalently bound to $X_4$, the covalent bond forming a cyclic peptide.

24. A method of decreasing the body weight of a subject, comprising administering to the subject an effective amount of a cytokine regulatory agent, comprising $X_4$-$X_5$-(D) Phe-Arg-(D)Trp-$X_3$, wherein $X_4$ is

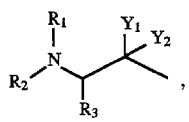

H, COCH$_3$, or absent;

$X_5$ is His, H, or COCH$_3$: and
$X_3$ is

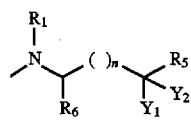

or R$_5$;

wherein Y$_1$ and Y$_2$ are independently a hydrogen atom, or are taken together to form a carbonyl or thiocarbonyl;

R$_1$ is H, COCH$_3$, C$_2$H$_5$, CH$_2$Ph, COPh, COOCH$_2$Ph, COO-t-butyl, CH$_2$CO-(polyethylene glycol) or A;

R$_2$ is H or COCH$_3$;

R$_3$ is a linear or branched alkyl group having 1 to 6 carbon atoms or a cyclic alkyl group having 3 to 6 carbon atoms;

R$_4$ is (CH$_2$)$_m$-CONH$_2$, (CH$_2$)$_m$-CONHR$_{21}$ or (CH$_2$)$_m$-CONHA;

R$_5$ is OH, OR$_3$, NH$_2$, SH, NHCH$_3$, NHCH$_2$Ph or A; and

R$_6$ is H or R$_3$;

and wherein "Ph" is C$_6$H$_5$, "m" is 1, 2 or 3, "n" is 0, 1, 2 or 3, and "A" is a carbohydrate having the general formula:

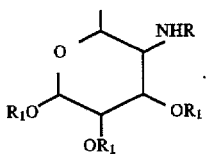

25. A method of increasing the oxygen consumption of a subject, comprising administering to the subject an effective amount of a cytokine regulatory agent, comprising $X_4$-$X_5$-(D)Phe-Arg-(D)Trp-$X_3$, wherein
$X_4$ is

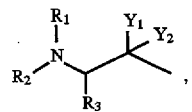

H, COCH$_3$, or absent;

$X_5$ is His, H, or COCH$_3$; and $X_3$ is

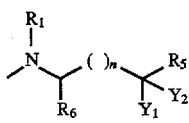

or R$_5$;

wherein Y$_1$ and Y$_2$ are independently a hydrogen atom, or are taken together to form a carbonyl or thiocarbonyl;

R$_1$ is H, COCH$_3$, C$_2$H$_5$, CH$_2$Ph, COPh, COOCH$_2$Ph, COO-t-butyl, CH$_2$CO-(polyethylene glycol) or A;

R$_2$ is H or COCH$_3$;

R$_3$ is a linear or branched alkyl group having 1 to 6 carbon atoms or a cyclic alkyl group having 3 to 6 carbon atoms;

R$_4$ is (CH$_2$)$_m$-CONH$_2$, (CH$_2$)$_m$-CONHR$_1$ or (CH$_2$)$_m$-CONHA;

R$_5$ is OH, OR$_3$, NH$_2$, SH, NHCH$_3$, NHCH$_2$Ph or A: and

R$_6$ is H or R$_3$;

and wherein "Ph" is C$_6$H$_5$, "m" is 1, 2 or 3, "n" is 0, 1, 2 or 3, and "A" is a carbohydrate having the general formula:

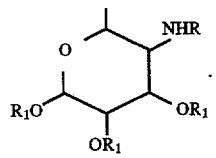

26. A method of enhancing cytokine activity in a subject having a condition characterized by altered or aberrant cytokine activity, comprising administering to the subject an effective amount of a cytokine regulatory agent selected from the group consisting of (cyclohexyl)Gly-Gln-His-(D) Phe-Arg-(D) Trp-Gly:

His- (D) Phe-Arg-(D) Trp-Gly;

His- (D) Phe-Arg- (D)Trp;

(D) Phe-Arg- (D) Trp; and

His- (D) Phe-Arg- (D) Trp(CH$_2$)-(NAc)Gly.

27. A method of enhancing cytokine activity in a subject having a condition characterized by altered or aberrant cytokine activity, comprising administering to the subject an effective amount of the cytokine regulatory agent cyclo(His-(D)Phe-Arg-(D)Trp).

28. A method of decreasing the body weight of a subject, comprising administering to the subject an effective amount of the cytokine regulatory agent Ac-Nle-Gln-His- (D) Phe-Arg- (D) Trp-Gly-NH$_2$.

29. A method of increasing the oxygen consumption of a subject, comprising administering to the subject an effective amount of the cytokine regulatory agent Ac-Nle-Gln-His- (D) Phe-Arg- (D) Trp-Gly-NH$_2$.

30. A method of increasing the levels of a cytokine in a subject, comprising administering to the subject an effective amount of the cytokine regulatory agent Ac-Nle-Gln-His- (D) Phe-Arg- (D) Trp-Gly-NH$_2$.

31. The method of claim 30, wherein said cytokine is IL-10.

* * * * *

UNITED STATES PATENT AND TRADEMARK OFFICE
CERTIFICATE OF CORRECTION

PATENT NO. : 5,726,156
DATED : March 10, 1998
INVENTOR(S) : Girten et al.

Page 1 of 3

It is certified that error appears in the above-identified patent and that said Letters Patent is hereby corrected as shown below:

Column 3,
Line 40, before the structure, please insert -- $X_1$ is --.
Line 40, after ", ", please insert -- H or $COCH_3$; --.
Line 46, before the structure, please insert -- $X_2$ is --
Line 46, after ";" please insert -- and --.
Line 53, before the structure, please insert -- $X_3$ is --
Line 53, after the structure, please insert -- or $R_5$; --.

Column 4,
Line 25, before the structure, please insert-- $X_4$ is --.
Line 25, after "," please insert -- H, $COCH_3$, or absent; --.
Line 33, before the structure, please insert -- $X_3$ is --.
Line 33, after the structure, please insert -- or R5; --.
Line 39, please replace "iS" with -- is --.

Column 15,
Line 47, please replace "GIy-$NH_2$" with -- Gly-$NH_2$ --.

Column 16,
Line 26, please replace "(D)TrP" with -- (D)Trp --.

Column 17,
Line 59, please replace "etal.," with -- et al., --.

Column 18,
Line 64, please replace "etal.," with -- et al., --.

Column 23,
Line 35, after "(iv)" please insert -- . --.

Column 25,
Line 16, please replace "inc.;" with -- Inc.; --.
Line 67, after "(IBMX" please insert -- ) --.

Column 26,
Line 4, please replace "$HC_1$" with -- HCl --.

UNITED STATES PATENT AND TRADEMARK OFFICE
CERTIFICATE OF CORRECTION

PATENT NO.   : 5,726,156
DATED        : March 10, 1998
INVENTOR(S)  : Girten et al.

It is certified that error appears in the above-identified patent and that said Letters Patent is hereby corrected as shown below:

Column 27,
Line 2, after "weight" please insert -- (32% --.
Line 46, please replace "In" with -- in --.

Column 29, claim 1,
Line 38, please replace ":" with -- ; --.

Column 30, claim 15,
Line 43, after COPh," please insert -- COOCH$_2$Ph, --

Column 31, claim 16,
Line 11, please replace "Hor" with -- H or --.
Line 37, please replace "C$_2$P$_5$" with -- C$_2$H$_5$ --.
Line 38, please replace "poiyethylene" with -- polyethylene --.
Line 38, please replace ":" with -- ; --.

Column 32, claim 17,
Lines 4 to 9, please replace

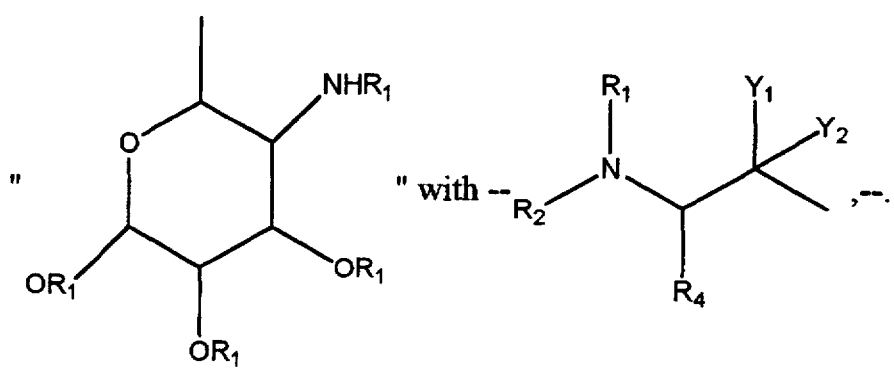

UNITED STATES PATENT AND TRADEMARK OFFICE
CERTIFICATE OF CORRECTION

PATENT NO. : 5,726,156
DATED : March 10, 1998
INVENTOR(S) : Girten et al.

It is certified that error appears in the above-identified patent and that said Letters Patent is hereby corrected as shown below:

Column 33, claim 25,
Line 59, please replace "$R_3$" with -- $R_4$ --.

Column 34, claim 25,
Line 19, please replace ":" with -- ; --.

Signed and Sealed this

Twenty-second Day of January, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 5,726,156
DATED : March 10, 1998
INVENTOR(S) : Girten et al.

It is certified that error appears in the above-identified patent and that said Letters Patent is hereby corrected as shown below:

Column 3,
Line 40, before the structure, please insert -- $X_1$ is --.
Line 40, after ", ", please insert -- H or $COCH_3$; --.
Line 46, before the structure, please insert -- $X_2$ is --.
Line 46, after ";" please insert -- and --.
Line 53, before the structure, please insert -- $X_3$ is --.
Line 53, after the structure, please insert -- or $R_5$; --.

Column 4,
Line 25, before the structure, please insert-- $X_4$ is --.
Line 25, after "," please insert -- H, $COCH_3$, or absent; --.
Line 33, before the structure, please insert -- $X_3$ is --.
Line 33, after the structure, please insert -- or $R_5$; --.
Line 39, please replace "iS" with -- is --.

Column 15,
Line 47, please replace "GIy-$NH_2$" with -- Gly-$NH_2$ --.

Column 16,
Line 26, please replace "(D)TrP" with -- (D)Trp --.

Column 17,
Line 59, please replace "etal.," with -- et al., --.

Column 18,
Line 64, please replace "etal.," with -- et al., --.

Column 23,
Line 35, after "(iv)" please insert -- . --.

Column 25,
Line 16, please replace "inc.;" with -- Inc.; --.
Line 67, after "(IBMX" please insert -- ) --.

Column 26,
Line 4, please replace "$HC_1$" with -- HCl --.

UNITED STATES PATENT AND TRADEMARK OFFICE
CERTIFICATE OF CORRECTION

PATENT NO. : 5,726,156
DATED : March 10, 1998
INVENTOR(S) : Girten et al.

It is certified that error appears in the above-identified patent and that said Letters Patent is hereby corrected as shown below:

Column 27,
Line 2, after "weight" please insert -- (32% --.
Line 46, please replace "In" with -- in --.

Column 29, claim 1,
Line 38, please replace ":" with -- ; --.

Column 30, claim 15,
Line 43, after "COPh," please insert -- COOCH$_2$Ph, --

Column 31, claim 16,
Line 11, please replace "Hor" with -- H or --.
Line 37, please replace "C$_2$P$_5$" with -- C$_2$H$_5$ --.
Line 38, please replace "poiyethylene" with -- polyethylene --.
Line 38, please replace ":" with -- ; --.

Column 32, claim 17,
Lines 4 to 9, please replace

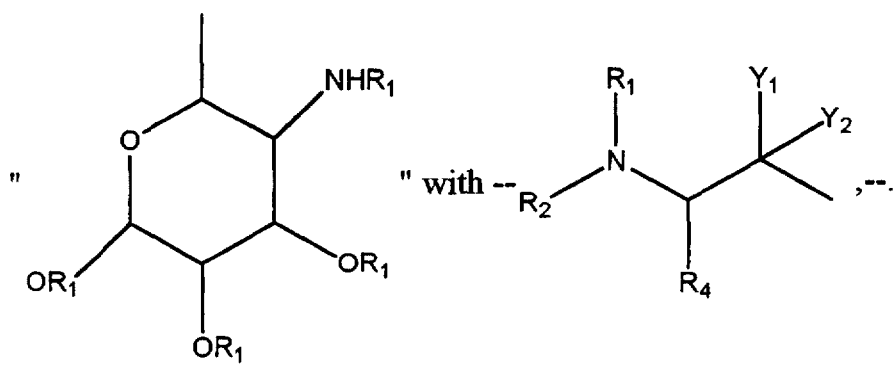

UNITED STATES PATENT AND TRADEMARK OFFICE
CERTIFICATE OF CORRECTION

PATENT NO. : 5,726,156
DATED : March 10, 1998
INVENTOR(S) : Girten et al.

Page 3 of 3

It is certified that error appears in the above-identified patent and that said Letters Patent is hereby corrected as shown below:

Column 33, claim 25,
Line 59, please replace "$R_3$" with -- $R_4$ --.

Column 34, claim 25,
Line 19, please replace ":" with -- ; --.

This certificate supersedes Certificate of Correction issued January 22, 2002.

Signed and Sealed this

Thirtieth Day of April, 2002

Attest:

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO.    : 5,726,156
DATED         : March 10, 1998
INVENTOR(S)   : Girten et al.

It is certified that error appears in the above-identified patent and that said Letters Patent is hereby corrected as shown below:

Column 32,
Line 26, please replace ":" with -- ; --.
Line 32, please replace "or(CH$_2$)$_m$-" with -- or (CH$_2$)$_m$- --.
Line 34, please replace ":" with -- ; --.
Line 37, please replace "is," with -- is --.

Column 33,
Line 6, please replace "R$_3$" with -- R$_4$ --.
Line 22, please replace ":" with -- ; --.
Line 30, please replace "(CH$_2$)$_m$-CONHR$_{21}$" with -- (CH$_2$)$_m$-CONHR$_1$ --.
Line 48, please replace "subject,comprising" with -- subject, comprising --.
Line 59, please replace "R$_3$" with -- R$_4$ --.

Column 34,
Line 19, please replace ":" with -- ; --.

This certificate supersedes Certificate of Correction issued April 30, 2002.

Signed and Sealed this

Third Day of September, 2002

Attest:

Attesting Officer

JAMES E. ROGAN
Director of the United States Patent and Trademark Office